United States Patent [19]

Smith et al.

[11] Patent Number: 5,208,144
[45] Date of Patent: May 4, 1993

[54] METHOD FOR DETECTION OF HUMAN DNA CONTAINING THE GENE ENCODING LOW DENSITY LIPOPROTEIN RECEPTOR

[75] Inventors: John A. Smith, Brookline; Raktima Raychowdhury; John L. Niles, both of Cambridge, all of Mass.

[73] Assignee: The General Hospital Corporation, Boston, Mass.

[21] Appl. No.: 396,697

[22] Filed: Aug. 22, 1989

Related U.S. Application Data

[63] Continuation-in-part of Ser. No. 313,682, Feb. 22, 1989, abandoned, which is a continuation-in-part of Ser. No. 235,211, Aug. 23, 1988, abandoned.

[51] Int. Cl.$^5$ .................. C12Q 1/68; C07H 15/12; C07H 17/00; C12N 15/00
[52] U.S. Cl. ...................................... 435/6; 536/23.5; 536/23.4; 935/77; 935/78
[58] Field of Search ................. 435/6; 536/27; 935/77, 935/78

[56] References Cited

U.S. PATENT DOCUMENTS 4,743,679 5/1988 Cohen et al. ................. 530/350
4,745,060 5/1988 Brown et al. ................. 435/172.3

FOREIGN PATENT DOCUMENTS 0026551 4/1981 European Pat. Off. ..
0177915 4/1986 European Pat. Off. ..
0234888 9/1987 European Pat. Off. ..
WO85/00369 1/1985 PCT Int'l Appl. ..
WO86/04090 7/1986 PCT Int'l Appl. ..

OTHER PUBLICATIONS

Edgington, T. S. et al., *J. Exp. Med.* 127:555-572 (1968).
Naruse, T. et al., *Lab. Invest.* 33:141-146 (1975).
Kerjaschki, D. et al., *Proc. Nat'l. Acad. Sci. USA* 79: 5557-5561 (1982).
Kerjaschki, D. et al., *J. Exp. Med.* 157:667-686 (1983).
Kerjaschki, D. et al., *Kidney Internat.* 30:229-245 (1986).
Makker, S. P. et al., *Lab. Invest.* 50:287-293 (1984).
Singh, A. K. et al. *Immunology* 59:451-458 (1986).
Singh, A. K. et al., *Clin. Immunol. Immunopathol.* 48: 61-77 (1988).
Andres, G. et al., *Lab. Invest.* 55:510-520 (1986).
Van Damme, J. S. et al., *Lab. Invest.* 38:502-510 (1978).
Couser, W. G. et al., *J. Clin. Invest.* 62:1275-1287 (1978).
Bhan, A. K. et al., *Lab. Invest.* 53:421-432 (1985).
Kamata, K. et al., *J. Immunol.* 135:2400-2408 (1985).
Wong, W. W. et al., *Proc. Nat'l. Acad. Sci. USA* 82: 7711-7715 (1985).
Natori, Y. et al., *Clin. Exp. Immunol.* 69:33-40 (1987).
Yamamoto, T. et al., *Cell* 39:27-28 (1984).
Gray, A. et al., *Nature* 303:722-725 (1983).
Scott, J. et al., *Science* 221:236-240 (1983).
Ullrich, A. et al., *Nature* 309:418-425 (1984).
Durkin, M. E. et al., *J. Cell Biol.* 107:2749-2756 (1988 Dec.).
Herz, J. et al., *EMBO J.* 7:4119-4127 (1988).
Ronco, P. et al., (*J. Immunol.* 136:125-130 (1986)).
Hsu, L. C. et al. (*Proc. Natl. Acad. Sci. USA* 82: 3771-3775 (1985).
European Search Report for Application EP89115331.
Camussi, G. et al., *J. Immunol.* 135:2409-2416 (1985).
Suggs, S. V. et al., *Proc. Natl. Acad. Sci. USA* 78:6613-6617 (1981).
Brown, M. S. et al., *Science* 232:34-46 (1986).
Lehrman, M. A. et al., *Proc. Natl. Acad. Sci. USA* 83:3679-3683 (1986).
Hobbs, H. H. et al. *Proc. Natl. Acad. Sci. USA* 82:7651-7655 (1985).
Talmud, P. et al., *Atherosclerosis* 89:137-141 (1991).
Davis, C. G. et al., *Cell* 45:15-24 (1986).
Kotze, M. J. et al., *J. Med. Genet.* 27:298-302 (1990).
Loux, N. et al., *Hum. Genet.* 87:373-375 (1991).
Sambrook, J. et al., *Molecular Cloning, A Laboratory Manual*, vol. 2:11.7-11.8 (1989).
De Heer, E. et al., *Biol. Abstr.* 78(12):10334 (1984).
De Heer, E. et al., *Immunology* 52:743-752 (1984).

*Primary Examiner*—Margaret Moskowitz
*Assistant Examiner*—Mindy B. Fleisher
*Attorney, Agent, or Firm*—Sterne, Kessler, Goldstein & Fox

[57] ABSTRACT

A method for the detection of a genetic abnormality in the LDL receptor gene, by hybridization of such gene with a DNA sequence encoding gp330.

1 Claim, 15 Drawing Sheets

| Peak | Peptide Sequence |
|---|---|
| #53 | Met-Gly-Asp-Asn-Val-Met-Phe<br>Asp<br>Ala |
| #54 | Val-Leu-Val-Val-Asn-Pro-Trp-Leu-<br>Trp-Pro |
| #60 | Asn-Leu-Tyr-Trp-Thr-Asp-Tyr-Ala-Leu-Glu-(Thr)-Ile-Glu-<br>Ala<br>Trp |
| | Val-?-Lys-Ile-(Asp)- |
| #74 | Gly-Ile-Ala-Leu-?-Pro-?-Val-?-Tyr-Leu-Phe-Phe- |
| #77 | Leu-Tyr-Trp-Val-Asp-Ala-Phe-Phe-Asp-?-Ile- |

? = BLANK
( ) = QUESTIONABLE

FIG. 2

R—EcoRI, C—ClaI, A—AccI, P—PstI, H—HindIII

```
           10                    30                    50
GATGAGGAAAACTGCGTTCCTCGGGAGTGCTCAGAGAGCGAGTTTCGATGTGCTGATCAG
 D  E  E  N  C  V  P  R  E  C  S  E  S  E  F  R  C  A  D  Q
           70                    90                    110
CAATGCATCCCCTCTCGATGGGTCTGTGACCAAGAAAATGACTGTGGAGACAACTCGGAT
 Q  C  I  P  S  R  W  V  C  D  Q  E  N  D  C  G  D  N  S  D
           130                   150                   170
GAACGGGACTGTGAGATGAAGACTTGCCATCCTGAACATTTTCAGTGTACGAGTGGACAC
 E  R  D  C  E  M  K  T  C  H  P  E  H  F  Q  C  T  S  G  H
           190                   210                   230
TGTGTCGCCAAGGCCTTGGCATGCGATGGGAGGGCAGACTGTCTGGATGCGTCTGATGAA
 C  V  A  K  A  L  A  C  D  G  R  A  D  C  L  D  A  S  D  E
           250                   270                   290
TCTGCTTGTCCTACTCGCTTTCCCAACGGCACCTACTGCCCAGCCGCCATGTTCGAATGT
 S  A  C  P  T  R  F  P  N  G  T  Y  C  P  A  A  M  F  E  C
           310                   330                   350
AAAAACCACGTGTGCATCCAGTCGTTTTGGATATGTGATGGGGAAAATGACTGTGTCGAC
 K  N  H  V  C  I  Q  S  F  W  I  C  D  G  E  N  D  C  V  D
           370                   390                   410
GGTTCCGATGAGGAGATCCACCTGTGCTTCAACATTCCGTGTGAATCACCACAGCGATTC
 G  S  D  E  E  I  H  L  C  F  N  I  P  C  E  S  P  Q  R  F
           430                   450                   470
CGGTGTGACAACAGCCGCTGTGTTTATGGCCATCAGCTGTGCAATGGTGTGGATGACTGC
 R  C  D  N  S  R  C  V  Y  G  H  Q  L  C  N  G  V  D  D  C
           490                   510                   530
GGAGATGGAAGTGACGAGAAAGAAGAGCACTGTAGAAAACCAACCCACAAACCGTGCACA
 G  D  G  S  D  E  K  E  E  H  C  R  K  P  T  H  K  P  C  T
           550                   570                   590
GACACTGAATATAAGTGTAGCAATGGGAACTGCATTTCGCAGCACTACGTGTGTGATAAT
 D  T  E  Y  K  C  S  N  G  N  C  I  S  Q  H  Y  V  C  D  N
           610                   630                   650
GTGAATGACTGCGGAGACCTTTCTGATGAAACTGGTTGCAATCTAGGAGATAACAGAACG
 V  N  D  C  G  D  L  S  D  E  T  G  C  N  L  G  D  N  R  T
           670                   690                   710
TGTGCTGAAAACATATGTGAACAGAACTGTACCCAGCTGAGCAGCGGAGGCTTTATCTGC
 C  A  E  N  I  C  E  Q  N  C  T  Q  L  S  S  G  G  F  I  C
           730                   750                   770
TCCTGCAGACCCGGGTTCAAACCCAGTACTTTGGACAAAAATTCCTGTCAAGACATCAAT
 S  C  R  P  G  F  K  P  S  T  L  D  K  N  S  C  Q  D  I  N
           790                   810                   830
GAATGTGAGGAGTTTGGCATCTGCCCCCAGAGCTGTCGAAACAGCAAAGGAAGTTATGAA
 E  C  E  E  F  G  I  C  P  Q  S  C  R  N  S  K  G  S  Y  E
           850                   870                   890
```

FIG. 4

```
TGTTTCTGTGTCGATGGCTTCAAGTCTATGAGTACCCATTATGGAGAACGGTGTGCAGCT
 C  F  C  V  D  G  F  K  S  M  S  T  H  Y  G  E  R  C  A  A
       910            930              950

GATGGAAGCCCTCCTCTCTTGCTCCTGCCTGAGAATGTCCGAATCCGGAAGTACATACCT
 D  G  S  P  P  L  L  L  P  E  N  V  R  I  R  K  Y  I  P
       970            990              1010

CCTCTGAGAATGTTCTCAGAGTATCTGGAAGAGGAGGAGCATATCCAAACTATTGACTAT
 P  L  R  M  F  S  E  Y  L  E  E  E  E  H  I  Q  T  I  D  Y
       1030           1050             1070

GACTGGGATCCCGAGCACATAGGCCTCAGTGTTGTCTATTACACTGTGCTGGCACAGGGC
 D  W  D  P  E  H  I  G  L  S  V  V  Y  Y  T  V  L  A  Q  G
       1090           1110             1130

TCTCAATTCGGTGCTATCAAACGTGCCTACATTCCCAACTTTGAATCTGGTAGTAACAAT
 S  Q  F  G  A  I  K  R  A  Y  I  P  N  F  E  S  G  S  N  N
       1150           1170             1190

CCCATACGTGAAGTTGACCTGGGCTTGAAATATTTAATGCAGCCAGATGGATTAGCCGTG
 P  I  R  E  V  D  L  G  L  K  Y  L  M  Q  P  D  G  L  A  V
       1210           1230             1250

GACTGGGTCGGAAGGCATATTTACTGGTCAGATGCTAACAGCCAACGGATTGAGGTGGCT
 D  W  V  G  R  H  I  Y  W  S  D  A  N  S  Q  R  I  E  V  A
       1270           1290             1310

ACCCTCGATGGAAGGTACCGGAAGTGGCTGATCACCACCCAACTGGATCAGCCAGCTGCC
 T  L  D  G  R  Y  R  K  W  L  I  T  T  Q  L  D  Q  P  A  A
       1330           1350             1370

ATTGCTGTGAATCCTAAGCTAGGGCTTATGTTCTGGACTGACCAGGGAAAAACAGCCCAAA
 I  A  V  N  P  K  L  G  L  M  F  W  T  D  Q  G  K  Q  P  K
       1390           1410             1430

ATCGAGTCTGCCTGGATGAACGGGGAACATCGCAGCGTTCTGGTTTCTGAGAACCTTGGC
 I  E  S  A  W  M  N  G  E  H  R  S  V  L  V  S  E  N  L  G
       1450           1470             1490

TGGCCAAACGGTCTTTCCATAGATTACCTGAATGATGACCGGGTCTACTGGAGCGACTCC
 W  P  N  G  L  S  I  D  Y  L  N  D  D  R  V  Y  W  S  D  S
       1510           1530             1550

AAAGAAGATGTCATTGAAGCCATAAAATATGATGGGACTGACAGGAGACTTATCATAAAT
 K  E  D  V  I  E  A  I  K  Y  D  G  T  D  R  R  L  I  I  N
       1570           1590             1610

GAGGCGATGAAGCCCTTCAGTCTGGACATCTTCGAAGACAAGCTATACTGGGTAGCTAAG
 E  A  M  K  P  F  S  L  D  I  F  E  D  K  L  Y  W  V  A  K
       1630           1650             1670

GAAAAGGGAGAAGTGTGGAGACAAAATAAATTCGGGAAAGAGAACAAAGAGAAAGTGCTG
 E  K  G  E  V  W  R  Q  N  K  F  G  K  E  N  K  E  K  V  L
       1690           1710             1730
```

FIG. 4A

```
GTGGTGAACCCGTGGCTCACTCAAGTTCGAATCTTCCATCAACTGAGATACAATCAGTCA
 V  V  N  P  W  L  T  Q  V  R  I  F  H  Q  L  R  Y  N  Q  S
    1750          1770               1790

GTGTCCAACCCTTGCAAGCAGGTCTGTAGTCACCTCTGCCTGCTGAGACCAGGAGGCTAC
 V  S  N  P  C  K  Q  V  C  S  H  L  C  L  L  R  P  G  G  Y
    1810          1830               1850

AGCTGTGCCTGTCCCCAAGGCTCCGACTTCGTAACTGGCAGCACTGTCCAGTGTGATGCA
 S  C  A  C  P  Q  G  S  D  F  V  T  G  S  T  V  Q  C  D  A
    1870          1890               1910

GCCAGTGAACTTCCCGTCACCATGCCTCCCCCATGCAGGTGCATGCACGGAGGAAATTGC
 A  S  E  L  P  V  T  M  P  P  P  C  R  C  M  H  G  G  N  C
    1930          1950               1970

TATTTTGATGAGAATGAACTCCCCAAATGCAAGTGTTCCAGTGGCTATAGCGGAGAATAC
 Y  F  D  E  N  E  L  P  K  C  K  C  S  S  G  Y  S  G  E  Y
    1990          2010               2030

TGTGAGGTTGGGCTCTCGAGAGGCATCCCTCCAGGGACGACAATGGCTGTTCTGTTGACC
 C  E  V  G  L  S  R  G  I  P  P  G  T  T  M  A  V  L  L  T
    2050          2070               2090

TTCGTGATAGTCATCATTGTTGGAGCTCTGGTGCTTGTTGGACTCTTTCACTACAGGAAA
 F  V  I  V  I  I  V  G  A  L  V  L  V  G  L  F  H  Y  R  K
    2110          2130               2150

ACTGGCTCCCTCTTACCCACTCTGCCCAAGCTGCCAAGCCTAAGCAGCCTTGCCAAACCC
 T  G  S  L  L  P  T  L  P  K  L  P  S  L  S  S  L  A  K  P
    2170          2190               2210

TCTGAAAATGGAAATGGGGTGACGTTCAGGTCGGGGGCTGATGTGAACATGGACATCGGT
 S  E  N  G  N  G  V  T  F  R  S  G  A  D  V  N  M  D  I  G
    2230          2250               2270

GTGTCTCCTTTCGGCCCTGAGACAATTATTGACAGATCCATGGCGATGAATGAACACTTT
 V  S  P  F  G  P  E  T  I  I  D  R  S  M  A  M  N  E  H  F
    2290          2310               2330

GTCATGGAGGTGGGCAAGCAGCCTGTGATATTTGAAAACCCAATGTATGCAGCCAAGGAC
 V  M  E  V  G  K  Q  P  V  I  F  E  N  P  M  Y  A  A  K  D
    2350          2370               2390

AACACTTCCAAAGTGGCCCTGGCAGTTCAGGGGCCATCAACAGGCGCACAGGTGACTGTA
 N  T  S  K  V  A  L  A  V  Q  G  P  S  T  G  A  Q  V  T  V
    2410          2430               2450

CCAGAAAATGTGGAAAACCAGAATTATGGAAGGCCCATAGATCCTTCTGAGATAGTTCCA
 P  E  N  V  E  N  Q  N  Y  G  R  P  I  D  P  S  E  I  V  P
    2470          2490               2510

GAGCCAAAGCCAGCCTCCCCTGGAGCTGATGAAATTCAGGGCAAAAAATGGAACATCTTC
 E  P  K  P  A  S  P  G  A  D  E  I  Q  G  K  K  W  N  I  F
    2530          2550               2570
```

FIG. 4B

```
AAACGAAAACCCAAACAGACAACGAACATTGAGAACCCAATCTACGCAGAGATGGACAGT
 K  R  K  P  K  Q  T  T  N  I  E  N  P  I  Y  A  E  M  D  S
      2590                2610                2630

GAGGTAAAGGATGCTGTGCTGTGGCCCCCCCTCCGTCTCCTTCTCTCCCTGCCAAAGCTT
 E  V  K  D  A  V  L  W  P  P  L  R  L  L  L  S  L  P  K  L
    2650                2670                2690

CAAAAAGAAATTTGACTCCAGGCTACACTGCCACAGAAGACACCTTTAAAGACACTGCAA
 Q  K  E  I  *
      2710                2730                2750

ATCTCGTTAAAGAAGATTCCGACGTATAGCCTCGCCAGCTCTCTAGGGAACATTTAGACA
      2770                2790                2810

CTCACTTTTTGCACATATATTTTTTACAGACAAATGAAAAAGAAGTTAACATTCAATACT
      2830                2850                2870

TTATAAAAAAATATATTTTTCTCTGTTTGCCTATAATTGAAGGTGTGTCGTGTGTCTTTT
      2890                2910                2930

TTACTGATGCCACTTCATATTTTTACAATTATCACGGGCACTGTGTATATCTTGGCG
```

```
         10                      30                         50
GCCACACTTGCCCGCCGGATTTCACAAAATGCCAGACCACGAATATTTGTGTTCCCCGAG
  H  T  C  P  P  D  F  T  K  C  Q  T  T  N  I  C  V  P  R  A
         70                      90                        110
CTTTCTTGTGTGATGGAGACAATGACTGTGGAGACGGGAGTGACGAGAACCCCATTTACT
  F  L  C  D  G  D  N  D  C  G  D  G  S  D  E  N  P  I  Y  C
        130                     150                        170
GCGCCTCACACACATGCCGCAGCAACGAGTTCCAGTGCCTCTCCCCTCAGCGGTGTATTC
  A  S  H  T  C  R  S  N  E  F  Q  C  L  S  P  Q  R  C  I  P
        190                     210                        230
CAAGCTATTGGTTCTGTGACGGTGAAGCCGACTGTGCAGATGGCTCGGATGAACCTGACA
  S  Y  W  F  C  D  G  E  A  D  C  A  D  G  S  D  E  P  D  T
        250                     270                        290
CTTGTGGGCATTCTGTGAACACCTGCAGGGCCAGTCAGTTCCAGTGTGATAATGGCAGGT
  C  G  H  S  V  N  T  C  R  A  S  Q  F  Q  C  D  N  G  R  C
        310                     330                        350
GCATCTCAGGCAATTGGGTCTGTGATGGTGATAACGACTGTGGGGACATGAGTGACGAGG
  I  S  G  N  W  V  C  D  G  D  N  D  C  G  D  M  S  D  E  D
        370                     390                        410
ACCAGCGGCATCACTGTGAGCTTCAGAACTGTTCCAGCACTCAGTTTACCTGTGTCAACA
  Q  R  H  H  C  E  L  Q  N  C  S  S  T  Q  F  T  C  V  N  S
        430                     450                        470
GCAGACCTCCCAACAGGAGGTGCATCCCACAGTACTGGGTCTGTGACGGTGATGCGGACC
  R  P  P  N  R  R  C  I  P  Q  Y  W  V  C  D  G  D  A  D
```

FIG. 8

```
                10                      30                      50
CGCTTGGCCATCGATTGGAGTGCTTCACGATTGTACTGGGTAGATGCCTTTTTTGATAAG
 R  L  A  I  D  W  S  A  S  R  L  Y  W  V  D  A  F  F  D  K
                70                      90                     110
ATTGAACACAGCACCCTTGATGGTTTAGATAGAAAAAGGCTGGGCCATGTAGACCAGATG
 I  E  H  S  T  L  D  G  L  D  R  K  R  L  G  H  V  D  Q  M
               130                     150                     170
ACTCATCCATTTGGACTCACCGTTTTTAAAGATAATGTGTTCATAACAGACTGGAGACTG
 T  H  P  F  G  L  T  V  F  K  D  N  V  F  I  T  D  W  R  L
               190                     210                     230
GGTGCTATTATTCGAGTGAGGAAATCAGATGGTGGTGATATGACAGTTATTCGAAGAGGC
 G  A  I  I  R  V  R  K  S  D  G  G  D  M  T  V  I  R  R  G
               250                     270                     290
ATCAGCAGCGTAATGCACGTGAAAGCCTACGATGCTGACCTCCAGACTGGGTCTAACTAC
 I  S  S  V  M  H  V  K  A  Y  D  A  D  L  Q  T  G  S  N  Y
               310                     330                     350
TGCAGTCAGACCACCCACGCCAACGGTGACTGCAGCCACTTCTGCTTCCCGGTCCCGAAC
 C  S  Q  T  T  H  A  N  G  D  C  S  H  F  C  F  P  V  P  N
               370                     390                     410
TTCCAGCGGGTGTGTGGCTGTCCCTATGGAATGAAACTTCAGAGGGATCAAATGACTTGT
 F  Q  R  V  C  G  C  P  Y  G  M  K  L  Q  R  D  Q  M  T  C
               430                     450                     470
GAGGGAGACCCAGCCCGAGAGCCACCCACACAGCAGTGTGGCTCCCTCTCCTTTCCCTGC
 E  G  D  P  A  R  E  P  P  T  Q  Q  C  G  S  L  S  F  P  C
               490                     510                     530
AACAATGGCAAGTGTGTGCCCAGTTTCTTCCGCTGTGATGGAGTGGACGATTGCCATGAC
 N  N  G  K  C  V  P  S  F  F  R  C  D  G  V  D  D  C  H  D
               550                     570                     590
AACAGTGATGAGCATCAGTGCGGGGTGTTTAATAATACTTGCTCACCTTCGGCTTTCGCC
 N  S  D  E  H  Q  C  G  V  F  N  N  T  C  S  P  S  A  F  A
               610                     630                     650
TGCGTCCGCGGTGGACAGTGCATCCCTGGCCAGTGGCACTGTGACAGACAGAATGACTGT
 C  V  R  G  G  Q  C  I  P  G  Q  W  H  C  D  R  Q  N  D  C
               670                     690                     710
TTAGATGGCAGTGATGAGCAAAAATGCCCCACACATGCCACGTCGTCCACTTGCCCGTCC
 L  D  G  S  D  E  Q  K  C  P  T  H  A  T  S  S  T  C  P  S
               730                     750                     770
ACCTCCTTCACCTGCGACAATCACGTGTGCATCCCAAAAGACTGGGTCTGTGACACAGAC
 T  S  F  T  C  D  N  H  V  C  I  P  K  D  W  V  C  D  T  D
               790                     810                     830
AATGATTGCTCGGATGGCTCGGATGAAAAGAACTGCCAAGCTTCAGGGACCTGCCAGCCT
 N  D  C  S  D  G  S  D  E  K  N  C  Q  A  S  G  T  C  Q  P
               850                     870                     890
```

FIG.9A

```
ACACAGTTTCGGTGCCCTGACCACCGATGCATCAGCCCGCTGTATGTCTGTGATGGGGAC
 T  Q  F  R  C  P  D  H  R  C  I  S  P  L  Y  V  C  D  G  D
   910              930              950

AAGGACTGCGCGGATGGGTCTGATGAGGCGGGCTGTGTGTTAAACTGTACGAGTGCCCAG
 K  D  C  A  D  G  S  D  E  A  G  C  V  L  N  C  T  S  A  Q
   970              990              1010

TTCAAATGTGCCGATGGGAGTTCTTGCATTAACAGCAGGTACCGCTGCGATGGGGTTTAC
 F  K  C  A  D  G  S  S  C  I  N  S  R  Y  R  C  D  G  V  Y
   1030             1050             1070

GACTGCAGGGACAACTCTGACGAGGCAGGCTGCCCCACCAGGCCTCCCGGCATGTGCCAC
 D  C  R  D  N  S  D  E  A  G  C  P  T  R  P  P  G  M  C  H
   1090             1110             1130

CCGGATGAGTTCCAGTGCCAAGGAGACGGTACATGCATCCCTAACACCTGGGAGTGTGAC
 P  D  E  F  Q  C  Q  G  D  G  T  C  I  P  N  T  W  E  C  D
   1150             1170             1190

GGGCATCCAGACTGTATCCACGGGTCCGACGAGCACACTGGCTGTGTTCCTAAGACCTGC
 G  H  P  D  C  I  H  G  S  D  E  H  T  G  C  V  P  K  T  C
   1210             1230             1250

TCGCCGACTCATTTCCTCTGTGACAATGGAAACTGCATCTACAAAGCGTGGATCTGTGAT
 S  P  T  H  F  L  C  D  N  G  N  C  I  Y  K  A  W  I  C  D
   1270             1290             1310

GGGGACAATGATTGTAGGGATATGAGTGATGAGAAGGACTGTCCTACCCAGCCTTTTCAC
 G  D  N  D  C  R  D  M  S  D  E  K  D  C  P  T  Q  P  F  H
   1330             1350             1370

TGTCCTAGCACGCAGTGGCAGTGCCCGGGCTACAGCACCTGTATCAATCTGAGTGCCCTG
 C  P  S  T  Q  W  Q  C  P  G  Y  S  T  C  I  N  L  S  A  L
   1390             1410             1430

TGTGACGGCGTCTTTGACTGTCCGAATGGGACTGACGAGTCCCCACTTTGCAATCAAGAC
 C  D  G  V  F  D  C  P  N  G  T  D  E  S  P  L  C  N  Q  D
   1450             1470             1490

AGCTGCTCCCATTTTAATGGTGGCTGTACTCATCAGTGCATGCAAGGGCCCTTCGGAGCC
 S  C  S  H  F  N  G  G  C  T  H  Q  C  M  Q  G  P  F  G  A
   1510             1530             1550

ACATGCCTATGCCCATTAGGATACCAACTTGCCAATGATACCAAGACCTGTGAAGATATC
 T  C  L  C  P  L  G  Y  Q  L  A  N  D  T  K  T  C  E  D  I
   1570             1590             1610

AATGAGTGCGATATTCCAGGCTTCTGCAGCCAGCACTGCGTCAACATGAGAGGTTCCTTC
 N  E  C  D  I  P  G  F  C  S  Q  H  C  V  N  M  R  G  S  F
   1630             1650             1670

CGGTGCGCTTGTGATCCAGAATATACGCTGGAAAGTGATGGGCGGACTTGCAAAGTCACA
 R  C  A  C  D  P  E  Y  T  L  E  S  D  G  R  T  C  K  V  T
   1690             1710             1730

GGATCTGAAAATCCGTTGTTAGTTGTAGCAAGTCGTGACAAAATCATTGTGGACAACATC
 G  S  E  N  P  L  L  V  V  A  S  R  D  K  I  I  V  D  N  I
   1750             1770             1790
```

FIG. 9B

```
ACTGCCCACACGCACAATCTCTACTCGTTGGTCCAGGATGTTTCTTTTGTGGTTGCTCTT
 T  A  H  T  H  N  L  Y  S  L  V  Q  D  V  S  F  V  V  A  L
    1810           1830              1850

GATTTTGATTCAGTCACTGGTCGTGTCTTCTGGAGTGACTTACTGCAGGGTAAAACCTGG
 D  F  D  S  V  T  G  R  V  F  W  S  D  L  L  Q  G  K  T  W
    1870           1890              1910

AGTGTCTTTCAAAACGGAACAGACAAGAGAGTGGTCCATGACAGTGGCCTCTCTGTGACA
 S  V  F  Q  N  G  T  D  K  R  V  V  H  D  S  G  L  S  V  T
    1930           1950              1970

GAAATGATTGCAGTAGATTGGATTGGTCGCAACCTTTACTGGACGGACTATGCTCTTGAA
 E  M  I  A  V  D  W  I  G  R  N  L  Y  W  T  D  Y  A  L  E
    1990           2010              2030

ACAATCGAAGTTTCTAAAATTGATGGAAGTCACAGAACAGTACTGATCAGCAAAAATGTC
 T  I  E  V  S  K  I  D  G  S  H  R  T  V  L  I  S  K  N  V
    2050           2070              2090

ACAAAACCGAGGGGACTCGCGTTAGATCCCAGAATGGGTGATAATGTAATGTTTTGGTCT
 T  K  P  R  G  L  A  L  D  P  R  M  G  D  N  V  M  F  W  S
    2110           2130              2150

GACTGGGGCCATCACCCTCGCATTGAGCGAGCCAGCATGGATGGCACCATGCGCACAGTC
 D  W  G  H  H  P  R  I  E  R  A  S  M  D  G  T  M  R  T  V
    2170

ATTGTCCAGGAAAAGATCTAC
 I  V  Q  E  K  I  Y
```

FIG. 9C

METHOD FOR DETECTION OF HUMAN DNA CONTAINING THE GENE ENCODING LOW DENSITY LIPOPROTEIN RECEPTOR

CROSS REFERENCE TO RELATED APPLICATION

This application is a continuation-in-part of U. S. applications Ser. No. 07/313,682 filed Feb. 22, 1989, now abandoned which is a continuation-in-part of U.S. Ser. No. 07/235,211 filed Aug. 23, 1988.

FIELD OF THE INVENTION

The invention is in the field of recombinant genetics.

BACKGROUND OF THE INVENTION

Heymann nephritis is a well-known inducible rat model for human membranous glomerulonephritis (Heymann, W. et al., *Proc. Soc. Exp. Biol. Med.* 100:660 (1959); Heymann, W. et al., *Ann. N.Y. Acad. Sci.* 124:310 (1965)). Heymann nephritis is induced in the rat by immunizing with whole kidney homogenates incorporated in complete Freund's adjuvant. The antigen responsible for the disease (termed a "nephritogen") was found to be contained in a membrane preparation derived from tubular brush border regions of proximal convoluted tubules (known as Fx1A), and a more purified fraction (known as RTE$\alpha$5) was also reported to be nephritogenic (Edgington, T. S. et al., *J. Exp. Med.* 127:555 (1968)).

Other workers have identified nephritogenic glycoproteins in such kidney tubule preparations. For example, Naruse, T., et al., *Lab. Invest.* 33:141 (1975), described the isolation and purification of a 8.4S tubular glycoprotein which was nephritogenic. Kerjaschki and Farquhar isolated a glycoprotein having an estimated molecular weight of 330,000 daltons (gp330) which was a pathogenic antigen of Heymann nephritis. This brush border membrane glycoprotein was purified and characterized (Kerjaschki and Farquhar, *Kidney International* 30:229 (1986)). Other workers have reported that a 600,000 dalton glycoprotein (gp600), also a component of Fx1A, can induce this disease (Makker, S. P. and Singh, A. K., *Lab. Invest.* 50:287 (1984)). In total, four subunits of gp600 (gp330, gp140, gp110 and gp70) have been isolated and shown to be nephritogenic (Singh, A. K. and Schwartz, N. M., *Clin. Immunol. Immunopathol.* 48:61-77 (1988); Makker, S. P. and Singh, A. K., *Lab. Invest.* 50:287 (1984)). A 400 kD protein in the brush borders of human kidney tubules, which is similar to gp330, has also been identified (Kerjaschki, D. et al., *Am. J. Pathol.* 129: 183 (1987)).

The pathophysiological role of gp330 in "in situ" immune complex formatin, which results in glomerulonephritis, is not defined. However, it is believed that the deposit formation is initiated by the reaction of autoantibodies with gp330 on the surface of podocytes with the subsequent shedding of complexes into the basement membrane (Andres, G. et al., *Lab. Invest.* 55:520 (1986); Von Damme, B. J. C. et al., *Lab. Invest.* 38:502 (1978); Couser, W. G. et al., *J. Clin. Invest.* 62:1275 (1987)).

Gp330 is found on the apical plasmalemmal domain of said epithelial cells, in particular proximal renal tubules, glomerular podocytes, intestine, lung (type II pneumocytes), epidermis, and yolk sac (Doxsey, S. et al., *J Cell Biol.* 97:178a (1983); Chatelet, F. et al., *Am. J. Pathol.* 122:512 (1986)). Immuno-electron microscopic studies have shown that gp330 is concentrated in clathrin-coated pits (Bhan, A. K. et al., *Lab. Invest.* 53:421 (1986)). The coated pit appears to act as a molecular filter and mediates endocytic uptake of specific receptor proteins and their associated ligands. It is assumed that gp330, like a number of membrane receptors, is concentrated in coated pits and brings its ligand into the cell by a mechanisms known as "receptor-mediated endocytosis" (Brown, M. S. and Goldstein, J. L., *Science* 53:421 (1986); Goldstein, J. L. et al., *Nature* 270:679 (1979)).

Despite the advances provided by the study of Heymann nephritis, a need continues to exist for plentiful sources of polypeptides and glycoproteins implicated in autoimmune kidney disease to allow the development of diagnostic tools and novel forms of therapy for human membranous glomerulonephritis and other conditions.

SUMMARY OF THE INVENTION

The invention relates to a cloned gene which encodes gp330 of the renal tubular brush border preparation, Fx1A, or to a functional derivative thereof, and to the gp330 protein and its functional derivatives.

The invention also relates to vectors comprising the cloned gene of the invention, hosts transformed with the vectors of the invention, and the process for producing the protein by recombinant techniques.

DESCRIPTION OF THE FIGURES

FIG. 2 depicts the amino acid sequence of five tryptic peptides derived from gp330.

FIGS. 4, 4A, 4B, and 4C depict the DNA sequence of the 2.90 kb gp330 DNA fragment and the amino acid sequence expressed therefrom. This sequence was obtained from two overlapping 2.4 kb clones. The 29 amino acid transmembrane segment is singly underlined. The stop codon is doubly underlined.

FIGS. 6 and 6A depict a comparison of the amino acid sequences of rat gp330, human $LDL_R$ and mouse $EGF_p$.

FIG. 8 depicts the DNA sequence of a 480 base pair gp330 DNA fragment and the amino acid sequence expressed therefrom. The sequence encoded from base pair 122 to 235 and from 245 to 361 each consist of an approximately 40-amino acid cysteine-rich stretch which is homologous to the LDL receptor ligand binding domain (see FIG. 6). This region is repeated at least 14 times in the gp330 DNA and 7 times in the LDL receptor gene. Two segments each containing 5 cysteine residues, also related to the LDL receptor ligand binding domain are found between base pairs 1-109 and 337-480.

FIGS. 9A, 9B, and 9C depict the DNA sequence of an approximately 2.2 kb gp330 DNA fragment, and the amino acid sequence encoded therefrom. This sequence, derived from the sequence of a 1.4 kb clone and an overlapping 1.2 kb clone (FIG. 5), encodes three cysteine-rich segments that are homologous to the LDL-receptor binding domain (see FIGS. 5 and 6).

DESCRIPTION OF THE PREFERRED EMBODIMENTS

Figure 1:
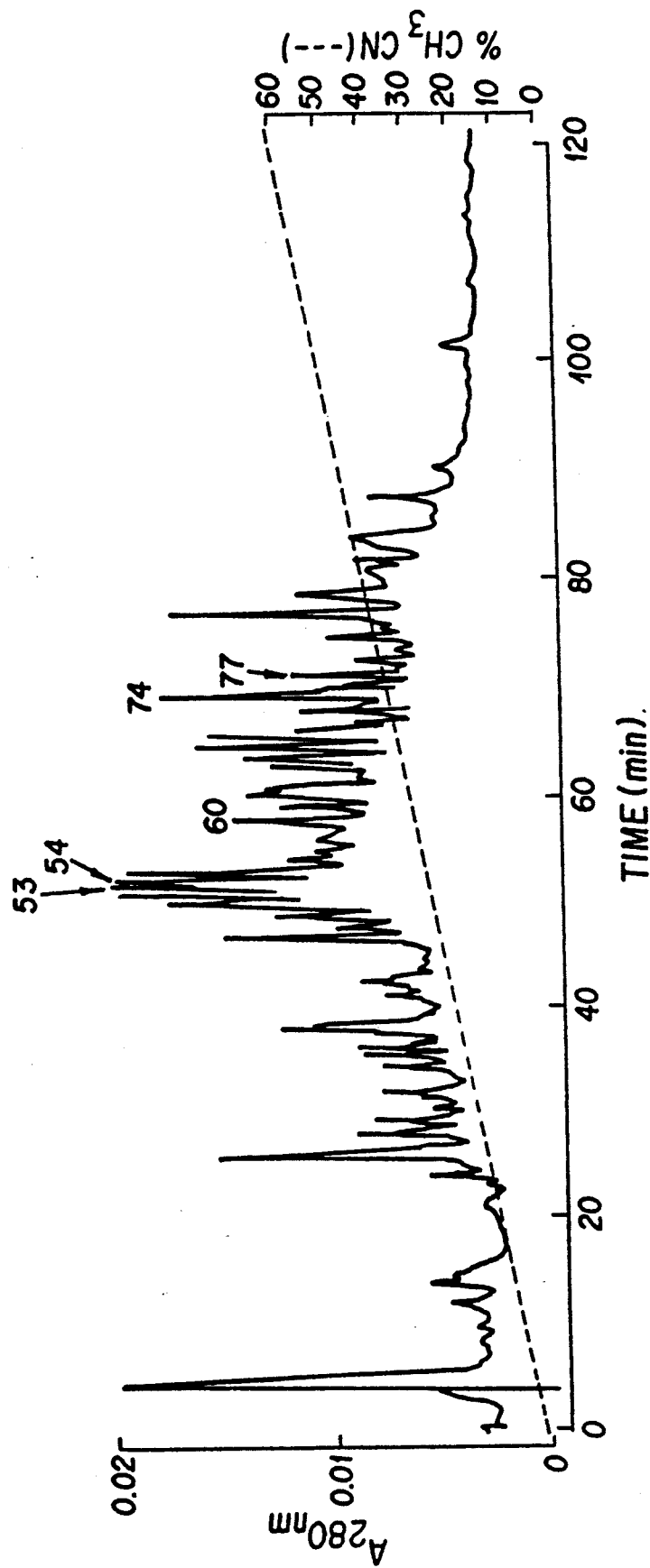
FIG. 1 depicts an HPLC trace of gp330 tryptic peptides separated by reverse phase HPLC.

The invention relates to a cloned gene which encodes the gp330 antigen of Fx1A or a functional derivative thereof. The invention also relates to vectors comprising the cloned genes of the invention, hosts transformed with the vectors of the invention, and the proteins expressed therefrom. The invention also provides for methods of treating various pathophysiological conditions in an animal by administering a pharmaceutical composition comprising gp330, or a functional derivative thereof. The invention also takes advantage of the homology between the gene coding for gp330 and the receptor for low density lipoprotein ($LDL_R$) and provides methods for molecular diagnosis and study of diseases related to abnormalities in the genes controlling $LDL_R$ production and function, such as, for example, Familial Hypercholesterolemia (FH).

The purified gp330 antigen has an apparent molecular weight of 440,000 on sodium dodecyl sulfate—polyacrylamide gel electrophoresis (SDS-PAGE). Therefore, by the term "gp330" is meant the glycoprotein from the renal tubule fraction of normal rat kidneys from the SpragueDawley or the Lewis strain having a band on SDS-PAGE corresponding to $M_r=440$ kD. The homologous molecule from other strains of rats may have similar but variant molecular weights, as is well known in the art.

A "functional derivative" of gp330 is a compound which possesses a biological structure or functional biological activity that is substantially similar to gp330. The term "functional derivative" is intended to include "fragments," "variants," "analogs," or "chemical derivatives" of gp330. The term "functional derivative" is also intended to include glycoproteins homologous to gp330 which are present in other species, in particular, in humans, and which are the targets of antibodies in autoimmune nephritis. A "fragment" of gp330 refers to any polypeptide or glycopeptide subset of the molecule. A "variant" of gp330 refers to a molecule substantially similar in structure and function to either the entire molecule, or to a fragment thereof.

A molecule is said to be "substantially similar" to another molecule if both molecules have substantially similar structures or if both molecules possess substantially similar biological activity. Thus, provided that two molecules possess substantially similar activity, they are considered "variants" as that term is used herein even if the complete structure of one of the molecules is not contained within the structure of the other or if the sequence of amino acid residues is not identical. An "analog" of gp330 refers to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, receptor or ligand binding, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

As used herein, the term "substantially pure" or "substantially purified" is meant to describe a protein which is substantially free of any compound normally associated with the protein in its natural state, i.e., free of other proteins and carbohydrate components. The term is further meant to describe a protein which is homogeneous by one or more criteria of purity or homogeneity used by those of skill in the art. For example, substantially pure gp330 will show constant and reproducible characteristics within standard experimental deviations for parameters such as molecular weight, appearance on a chromatographic medium, etc. The terms "substantially pure" or "substantially purified" are not meant to exclude artificial or synthetic mixtures of the protein with other compounds. Furthermore, the terms are not meant to exclude the presence of minor impurities which do not interfere with the biological activity of the protein, and which may be present, for example, due to incomplete purification.

The process for genetically engineering gp330 and functional derivatives thereof, according to the invention, is facilitated by the cloning of genetic sequences which are capable of encoding the protein and through the expression of such genetic sequences. As used herein, the term "genetic sequence" is intended to refer to a nucleic acid molecule (preferably DNA). Genetic sequences which are capable of encoding the gp330 and functional derivatives thereof may be derived from a variety of sources. These sources include genomic DNA, cDNA, synthetic DNA, and combinations thereof.

Genomic DNA may or may not include naturally occurring introns. Moreover, such genomic DNA may be obtained in association with the 5' promoter region of the gp330 gene sequences. To the extent that a host cell can recognize the transcriptional regulatory and translational initiation signals associated with the expression of the protein, the region 5' may be retained and employed for transcriptional and translational initiation regulation.

cDNA may be cloned and the resulting clones screened with an appropriate probe for cDNA coding for the desired sequences. Once the desired clone or clones has been isolated, the cDNA may be manipulated in substantially the same manner as the genomic DNA. However, cDNA will not contain introns or intervening sequences.

Isolation of DNA encoding gp330 may be achieved by a number of methods. For example, the DNA may be extracted and purified from suitable cells by means well known in the art. The DNA is then cleaved into linear fragments, any one of which may contain the gene which encodes gp330 or fragments thereof. Such fragmentation is achieved using nuclease enzymes such as, for example, restriction endonucleases which cleave DNA at specific base sequences. Linear DNA fragments then are separated according to size by standard techniques. Such recombinant DNA techniques may be performed as described by Maniatis, T. et al., *Molecular*

*Cloning: A Laboratory Manual,* Cold Spring Harbor Laboratory, Cold Spring Harbor, N.Y. (1982).

Alternatively, it is possible to isolate DNA encoding gp330 or fragments thereof by isolating mRNA which codes for gp330 (or fragments thereof) and producing cDNA therefrom using reverse transcriptase.

A preferred method for cloning the gp330 gene entails determining the amino acid sequence of the protein or of fragments thereof, following purification of the gp330 protein. Such purification is preferably performed using affinity chromatography with polyclonal or monoclonal antibodies. The protein can be further purified using preparative SDS-PAGE and electroelution.

Although it is possible to determine the entire amino acid sequence of the protein, it is preferable to determine the sequence of peptide fragments. Gp330 is cleaved with cyanogen bromide or with proteinases such as papain, chymotrypsin, or trypsin (Oike, Y., et al., *J. Biol. Chem.* 257:9751-9758 (1982); Liu, C., et al., *Int. J. Pept. Protein Res.* 21:209-215 (1983)). The resulting peptides are separated by reverse-phase high performance liquid chromatography (HPLC) and subjected to amino acid sequencing, preferably, by automated sequenators.

The sequence of amino acid residues in a peptide is designated herein either by their commonly employed three-letter or single-letter designations which may be found in textbooks such as *Biochemistry,* Lehninger, A., Worth Publishers, New York (1970). When the amino acid sequence is listed horizontally, the amino-terminus is intended to be on the left end, the carboxy-terminus is intended to be at the right end, and the amino acid residues may be separated by hyphens. Such hyphens are intended solely to facilitate the presentation of a sequence and are not to be construed as indicating chemical bonds.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene,* 3rd Ed., W. A. Benjamin, Inc., Menlo Park, Calif. (1977), pp. 356-357). The peptide fragments are analyzed to identify sequences of amino acids which may be encoded by oligonucleotides having the lowest degree of degeneracy. This is accomplished by identifying sequences that contain amino acids which are encoded by only a single codon.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene, only one member of the set contains the actual nucleotide sequence present in the gene. Because this member is present within the set, and is capable of hybridizing to DNA even in the presence of the other members of the set, it is possible to employ an unfractionated set of oligonucleotides in the same manner in which one would employ a single oligonucleotide to clone the gene encoding the peptide. Deoxyinosine may also be used as an "ambiguous codon" to reduce the degree of degeneracy. Ohtsuka, E. et al., *J. Biol. Chem.* 260:2605 (1985).

Using the genetic code (Watson, J. D. et al., *Molecular Biology of the Gene,* 4th Ed., Benjamin/Cummings Publishing Co., Menlo Park, Calif. (1987)), one or more different oligonucleotides can be identified, each of which would be capable of encoding gp330. The probability that a particular oligonucleotide will, in fact, constitute the actual gp330 coding sequence can be estimated by considering abnormal base pairing relationships and the frequency with which a particular codon is actually used (to encode a particular amino acid) in eukaryotic cells. Using such "codon usage rules," as disclosed by Lathe, R., et al., *J. Molec. Biol.* 183:1-12 (1985), a single oligonucleotide, or a set of oligonucleotides, that contains a theoretical "most probable" nucleotide sequence capable of encoding the gp330 sequences is identified.

The oligonucleotide, or set of oligonucleotides, containing the theoretical "most probable" sequence capable of encoding the gp330 gene fragments, optionally containing deoxyinosine, is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the gp330 gene from a genomic DNA or cDNA preparation (Maniatis, T., et al., *Molecular Cloning A Laboratory Manual,* Cold Spring Harbor Press, Cold Spring Harbor, N.Y. (1982).

Thus, in summary, the actual identification of a gp330 fragment amino acid sequence permits the identification of a theoretical "most probable" DNA sequence, or a set of such sequences, capable of encoding such a peptide. By constructing an oligonucleotide or set of oligonucleotides complementary to this theoretical sequence or "most probable" sequences, one obtains a DNA molecule or set of molecules capable of functioning as a probes to identify and isolate the gp330 gene.

A suitable oligonucleotide, or set of oligonucleotides, which is capable of encoding a fragment of the gp330 gene (or which is complementary to such an oligonucleotide, or set of oligonucleotides) is identified using the above-described procedure, synthesized, and hybridized by means well known in the art, to a DNA preparation derived from cells which are capable of expressing the gp330 gene. The source of DNA or cDNA used will preferably have been enriched for gp330 sequences. Such enrichment can most easily be obtained from cDNA obtained by extracting RNA from cells which expressed high levels of the gp330 gene. Those members of the above-described DNA library which are found to be capable of such hybridization are then analyzed to determine the extent and nature of the gp330 encoding sequences which they contain.

Techniques of nucleic acid hybridization are disclosed by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach.* IRL Press, Washington, DC (1985)), both of which are herein incorporated by reference.

To facilitate the detection of the desired gp330 coding sequence, the above-described DNA probe may be labeled with a detectable group. Such detectable group can be any material having a detectable physical or chemical property. Such materials have been well-developed both in the immunoassay and in the nucleic acid hybridization fields. In general, most any label useful in such methods can be used in the present invention. Particularly useful are enzymatically active groups, such as enzymes (see *Clin. Chem.* 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see *Clin. Chem.* 25:353 (1979)); chromophores; luminescers such as chemiluminescers and bioluminescers (see *Clin. Chem.* 25:512 (1979)); specifically bindable ligands; proximal interacting pairs; and radioisotopes such as $3_H$, $35_S$, $32_P$, $125_I$ and $14_C$. Such labels and labeling pairs are detected either on the basis of their endogenous physical properties (e.g. fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the such enzymes include, but are not limited to, beta-galactosidase, alkaline phosphatase and peroxidase.

Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S. et al., *Eur. Mol. Biol. Organ. J.* 4:2519–2524 (1985)), the human estrogen receptor (Walter, P. et al., *Proc. Natl. Acad. Sci. USA* 82:7889–7893 (1985)), tissue plasminogen activator (Pennica, D. et al., *Nature* 301:214–221 (1983)) and human placental alkaline phosphatase (Kam, W. et al., *Proc. Natl. Acad. Sci. USA* 82:8715–8719 (1985)).

A DNA sequence encoding gp330 or its functional derivatives may be recombined with DNA comprising a DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., suora. and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An "operable linkage" is a linkage in which the regulatory DNA sequences and the DNA sequence sought to be expressed are connected in such a way as to permit gene expression. The precise nature of the regulatory regions needed for gene expression may vary from organism to organism, but generally include a promoter region which, in prokaryotes, contains both the promoter (which directs the initiation of RNA transcription) as well as the DNA sequences which, when transcribed into RNA, will signal the initiation of protein synthesis. Such regions normally include those 5'-noncoding sequences involved with initiation of transcription and translation, such as the TATA box, capping sequence, CAAT sequence, and the like.

If desired, the non-coding region 3' to the coding sequence may be obtained by the above-described methods. This region may be retained for its transcriptional termination and polyadenylation regulatory sequences. Thus, by retaining the 3'-region naturally contiguous to the protein-coding sequence, the transcriptional termination signals may be provided. Where the transcriptional termination signals are not satisfactorily functional for expression in a particular host cell, then a 3' region functional in that host cell may be substituted.

Two DNA sequences (e.g. a promoter region sequence and a gp330-coding sequence) are said to be operably linked if the nature of the linkage between the two DNA sequences does not: (1) result in the introduction of a frame-shift mutation, (2) interfere with the ability of the promoter region sequence to direct the transcription of the gp330 gene, or (3) interfere with the ability of the gp330 gene sequence to be transcribed under control of the promoter region sequence. Thus, a promoter region would be operably linked to a DNA sequence if the promoter were capable of effecting transcription of that DNA sequence.

To express the protein, transcriptional and translational signals recognized by an appropriate host are necessary.

The present invention encompasses the expression of the gp330 protein (or a functional derivative thereof) in either prokaryotic or eukaryotic cells. Preferred prokaryotic hosts include bacteria such as *E. coli, Salmonella typhimurium. Serratia marcescens. Bacillus* species, *Streptomyces* species, *Pseudomonas* species, etc. The most preferred prokaryotic host is *E. coli*. When expressed in such bacterial hosts, gp330 will not be glycosylated. The prokaryotic host must be compatible with the replicon and control sequences in the expression vector or plasmid.

To express the gp330 protein (or a functional derivative thereof) in prokaryotic cells, it is necessary to operably link the gp330-coding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pPR325, etc. Examples of inducible prokaryotic promoters include the major right and left promoters of bacteriophage λ (PL and PR), the tro. recA. lacZ. lacI. and gal promoters of *E. coli* the α-amylase (Ulmanen, I., et al., *J. Bacteriol.* 162:176–182 (1985)) and the α-28-specific promoters of *B. subtilis* (Gilman, M. Z., et al., Gene 32 11–20 (1984)), the promoters of the bacteriophages of *Bacillus* (Gryczan, T. J., In: *The Molecular Biology of the Bacilli.* Academic Press, Inc., N.Y. (1982)), and *Streptomyces* promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream of the coding sequence. Ribosome binding sites, such as the Shine-Delgarno sequence, are disclosed, for example, by Gold, L., et al. (*Ann. Rev. Microbiol.* 35:365–404 (1981)).

Preferred eukaryotic hosts include yeast, fungi, mammalian cells (especially human cells) either in vivo. or in tissue culture. Mammalian cells provide post-translational modifications to protein molecules including glycosylation at correct sites and correct three-dimensional folding. Mammalian cells which may be useful as hosts include cells of fibroblast origin such as VERO or CHO-KI, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing.

For a mammalian host, several possible vector systems are available for the expression of gp330. A wide variety of transcriptional and translational regulatory sequences may be employed, depending upon the nature of the host cell. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from expressed mammalian genes such as those for actin, collagen, myosin, etc., may be employed. Transcriptional initiation regulatory signals may be selected which allow for repression or activation, so that expression of the genes can be modulated. Of interest are regulatory signals which are temperature-sensitive so that varying temperature can be used to repressed or initiate expression, or signals that are subject to chemical regulation, e.g. metabolites.

Yeast cells provide substantial advantages as host cells due to their ability to carry out post-translational peptide modifications including glycosylation. A number of recombinant DNA strategies exist which utilize strong promoter sequences and high copy number of plasmids which can be utilized for production of the desired proteins in yeast. Yeast cells recognize leader sequences on cloned mammalian gene products and secrete peptides bearing leader sequences (i.e., pre-peptides).

Any of a series of yeast gene expression systems incorporating promoter and termination elements from the actively expressed genes coding for glycolytic enzymes, produced in large quantities when yeast are grown in media rich in glucose, can be utilized. Known glycolytic genes can also provide very efficient transcriptional control signals. For example, the promoter and terminator signals of the phosphoglycerate kinase gene can be utilized.

As discussed above, expression of the gp330 protein in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter Benoist, C., et al., *Nature* (London) 290:304–310 (1981)); the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the gp330 protein (or a functional derivative thereof) does not contain any intervening codons which are capable of encoding methionine (i.e., AUG). The presence of such codons results either in formation of a fusion protein (if the AUG codon is in the same reading frame as gp330 encoding DNA sequence) or a frame-shift mutation (if the AUG codon is not in the same reading frame as the gp330 encoding sequence).

The gp330 coding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gp330 protein may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by introducing one or more markers which allow for selection of host cells which contain the expression vector. The marker may provide for prototropy to an auxotrophic host, resistance to biocides, e.g., antibiotics, or to heavy metals, such as copper or the like. The selectable marker gene can either be directly linked to the DNA gene sequences to be expressed, or introduced into the same cell by co-transformation or co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Mol. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColEI, pSCIOI, pACYC 184, πVX. Such plasmids are, for example, disclosed by Maniatis, T., et al. (In: *Molecular Cloning. A Laboratory Manual.* Cold Spring Harbor Press, Cold Spring Harbor, N.Y. (1982)). *Bacillus* plasmids include pC194, pC221, pT127, etc. Such plasmids are disclosed by Gryczan, T. (In: *The Molecular Biology of the Bacilli.* Academic Press, N.Y. (1982), pp. 307–329). Suitable Streptomyces plasmids include pIJIOI (Kendall, K. J., et al., *J. Bacteriol.* 169:4177–4183 (1987)), and streptomyces bacteriophages such as φC31 (Chater, K. F., et al., In: *Sixth International Symposium on Actinomycetales Biology,* Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jon. J. Bacteriol.* 33:729–742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J.

R., In: *The Molecular Biology of the Yeast Saccharomyces: Life Cycle and Inheritance.* Cold Spring Harbor Laboratory, Cold Spring Harbor, N.Y., p. 445–470 (1981); Broach, J. R., *Cell* 28 203–204 (1982); Bollon, D. P., et al., *J. Clin. Hematol. Oncol.* 10:39–48 (1980); Maniatis, T., In: *Cell Biology: A Comprehensive Treatise, Vol. 3, Gene Expression.* Academic Press, N.Y., pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of the gp330 protein, or in the production of a fragment of this protein. This can take place in the transformed cells as such, or following the induction of these cells to differentiate (for example, by administration of bromodeoxyuridine to neuroblastoma cells or the like).

The expressed protein may be isolated and purified in accordance with conventional conditions, such as extraction, precipitation, chromatography, affinity chromatography, electrophoresis, or the like.

The invention also relates to cloned genes which encode a fusion protein comprising gp330 or fragment thereof and a detectable enzyme such as beta-galactosidase. Methods for producing such fusion proteins are taught, for example, Bai, D. H. et al., *J. Biol. Chem.* 261:12395–12399 (1986), or Huynh, T. U. et al., in *DNA Cloning Techniques: A Practical Approach.* D. Glover (ed.), IRL Press, Oxford, 1985, pp. 49–77.

The gp330, functional derivative thereof, or fusion protein comprising gp330 or fragment thereof and a detectable enzyme may be isolated according to conventional methods known to those skilled in the art. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation.

The gp330 or functioned derivative thereof, or fusion protein comprising gp330 and a detectable enzyme, may be isolated by the use of anti-gp330 antibodies. The preparation of polyclonal rabbit anti-gp330 sera is disclosed in Example 2, below.

The above methods are, therefore, capable of identifying genetic sequences which are capable of encoding the gp330 protein or fragments of this protein. In order to further characterize such genetic sequences, it is desirable to express the proteins which these sequences encode, and confirm that they possess characteristics of gp330 peptides. Such characteristics may include the ability to bind anti-gp330 antibodies, the ability to elicit the production of anti-gp330 antibodies, or to carry out any of the biological functions of gp330, such as binding to a 76 kD serum protein which may be a ligand for gp330 (Kanalas, J. J. et al., *J. Immunol.* 141:4152 (1988)).

An antibody is said to be "capable of binding" a molecule if it is capable of specifically reacting with the molecule forming a noncovalent bond. The term "epitope" refers to that minimal portion of a larger structure can be recognized by an antibody resulting in binding. The epitope is thus defined in terms of the antibody which binds specifically to it and not to other epitopes on the larger structure. As used in the art, and herein, the term "antigen" includes a molecular structure comprising one, or more than one epitope. An "antigen," appropriately presented, is capable of inducing an animal to produce an antibody capable of binding "specifically" to an epitope of that antigen. The "specificity" is meant to indicate that the antibody will react, in a highly selective manner, with its corresponding antigen, and not with other antigens. Conversely, the specific antigen will not react with the multitude of other antibodies which may be evoked by other antigens.

The terms "antibody" (Ab) or "monoclonal antibody" (Mab) as used herein are meant to include intact molecules as well as fragments such as, for example, Fab and F(ab')2 fragments which are capable of binding an antigen. Fab and F(ab')2 fragments lack the Fc fragment of intact antibody, are cleared more rapidly from the circulation, and may show less non-specific tissue binding than an intact antibody molecule (Wahl et al., *J. Nucl. Med.* 24:316–325 (1983)).

The antibodies of the present invention may be prepared by any of a variety of methods. For example, cells expressing the gp330 protein, or a functional derivative thereof, can be administered to an animal. The sera of such immunized animals contain polyclonal antibodies that are capable of binding gp330.

In a more preferred embodiment, the antibodies of the present invention are monoclonal antibodies. Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas.* Elsevier, N.Y., pp. 563–681 (1981)). In general, such procedures involve immunizing a mouse or rat with gp330 antigen. Immune spleen cells are then removed and fused with cells of a suitable myeloma cell line. Any suitable myeloma cell line may be employed in accordance with the present invention. After fusion, the resulting hybridoma cells are selected in HAT medium, and then cloned by any of a number of known methods including that of limiting dilution as described by Wands, J. R., et al. (Gastroenterology 80:225–232 (1981), which reference is herein incorporated by reference). The cloned hybridoma cells so obtained are then assayed to identify clones which secrete antibodies capable of binding to gp330.

The DNA sequences which encode gp330, or a fragment thereof, may be used as DNA probes to isolate DNA coding for the analogous molecule in humans ("human analog") according to the above-described methods for isolation of rat gp330 with labeled probes. The human genes may then be cloned and expressed in a host to produce the human gp330 analog. This human protein or glycoprotein may then be used in diagnostic assays for detecting the corresponding autoantibody, and for therapeutic treatment of human membranous glomerulonephritis.

The invention also relates to a method of treating glomerulonephritis by coupling gp330, or a functional derivative thereof, to a polyphenol followed by immunization of an animal with the polyphenol-gp330, thereby resulting in the suppression of production of antibodies characteristic of glomerulonephritis and the prevention or amelioration of the symptoms of the disease. Such polyphenol conjugates may be prepared according to U.S. Pat. No. 4,702,907 to Becker et al., the disclosure of which is incorporated by reference herein in its entirety. In particular, this aspect of the invention relates to a method for the selective immunosuppression of anti-gp330 antibodies, wherein said antibody is not of the IgE isotype, which comprises:

(a) coupling a rutin-like polyphenol, having at least two hydroxyl groups, to gp330, or functional derivative thereof which is capable of inducing kidney nephritis, thereby forming a resultant product, provided that if only two hydroxyl groups are present in said polyphenol, the hydroxyl groups are in an ortho position to one another, and (b) injecting a sufficient amount of the resulting conjugate intradermally into a subject, leading to selective suppression of antibodies specific for gp330 or functional derivatives thereof.

It is also possible to utilize the gp330 or functional derivatives thereof to selectively remove gp330-reactive autoantibodies from the sera of an animal or human. In this embodiment, the gp330 or functional derivative thereof is immobilized on a solid phase support. The blood or serum of the animal is passed over this antigen-containing support to selectively remove autoantibodies. Methods of attaching peptides to surfaces are well-known and can be readily adapted for use in this invention. For example, a terminal amino acid of the polypeptide antigen can react with a reactive carbonyl, carboxylate, hydroxyl, or amino group of a solid polymer (or of a linking group attached to the polymer). Coating of unmodified peptide on plastic or glass surfaces can also be used to provide an immunologically reactive surface. See PCT Application Publication No. W086/04093 and U.S. Pat. No. 4,362,155.

Thus, in one embodiment, the invention includes a method to treat human membranous glomerulonephritis, which comprises.

(a) providing a solid support with immobilized gp330, a functional derivative thereof, or a human analog thereof, which is capable of binding with an autoantibody characteristic of human membranous glomerulonephritis; and (b) contacting the blood of a patient with the immobilized gp330, functional derivative thereof, or human analog thereof obtained in step (a)

whereby autoantibodies characteristic of human glomerulonephritis are removed from the blood. The removal of the gp330 antibodies from the patient's blood will decrease the formation of immune complexes in vivo and reduce the subsequent inflammatory disease.

The gp330 or functional derivative thereof produced according to this invention can also be directly administered to an afflicted host in order to perturb the formation of immune complexes. See PCT Application Publication No. W086/04093. Formation of immune complexes in an autoimmune state depends upon the presence of critical concentrations of the antigen and antibody; only at certain ratios will complex formation occur. This ratio is presumed to be optimal during periods of crisis in the autoimmune disease state. By the method of the present invention, injection of substantially pure gp330, or functional derivatives thereof, will alter the antigen-antibody ratio, and inhibit formation of new complexes. The reticuloendothelial system and phagocytes can successfully remove preformed immune complexes, and hinder the deposition of immune complexes in the kidney which leads to glomerulonephritis.

Synthetic, immunogenic gp330 peptides or functional derivatives thereof are useful therapeutically due to their ability to inhibit activation or function of antigen-specific helper and cytotoxic T-cells (Guillet, J.-G. et al., Science 235:865–870 (1987)) specific for gp330 or an analogous human membranous glomerulonephritis-associated antigen. Such immunogenic peptides are produced and selected by synthesizing nested sets of overlapping peptides and testing these in lymphocyte proliferation or cytotoxicity assays. Such therapy is aimed at reducing the T-cell responses operating in autoimmune membranous glomerulonephritis, including both cell-mediated immunity and the production of autoantibodies, which are regulated by antigen-specific T helper cells.

Synthetic peptides or truncated fusion proteins are also useful for localizing immunodominant sites of gp330 which B or T lymphocytes recognize. Certain of these antigenic peptides thus allow the detection of gp330-specific autoantibodies, and helper, cytotoxic, or suppressor T-cells which are specific for gp330 or related nephritogenic antigens.

It is also clear to those skilled in the art that the immunodiagnostic reagents of this invention, including both antigen and antibody preparations, are useful for identifying patients who may develop idiopathic autoimmune membranous glomerulonephritis, as well as to identify patients who might develop autoimmune membranous glomerulonephritis after receiving a renal allograft.

Surprisingly, the inventors have discovered that the protein sequence of gp330 shows homology with mouse epidermal growth factor precursor ($EGF_p$) and the human low density lipoprotein receptor ($LDL_R$). The $LDL_R$ includes 7 repeated stretches of about forty amino acids (Yamamoto, T. et al., Cell 39:27–38 (1984), herein incorporated by reference). A homologous sequence of about 40 amino acid is found in gp330, in at least fourteen separate repeats. The highly conserved cytoplasmic domain of the $LDL_R$ contains a seven amino acid sequence (NFDNPVY) which is similar to two sequences which have been identified in a liver asialoglycoprotein receptor. The protein sequence of gp330 reveals three such repeated sequences: the first starts at 2308 (FIG. 4) and has the sequence IFENPMY; the second starts at 2407 (FIG. 4) and has the sequence NVENQNY; the third starts at 2545 (FIG. 4) and has the sequence NIENPIY. These repeated sequences are believed to be important in the process of endocytosis. Thus, their recognition permits one to construct recombinant receptor proteins (containing one or more of these sequences) and to locate such artificial receptors in endocytic vesicles. Thus, by tying the repeat sequence(s) to the carboxyterminus of a molecule, it is possible to shuttle such a molecule into the endosome.

The gp330 molecule has a 188-amino acid long carboxy-terminal tail and differs from the $LDL_R$ in sequence from the end of the transmembrane region to the carboxy-terminus of the molecule.

The recognition of homology between gp330 and the EGF precursor peptide allows the use of gp330, or a functional derivative thereof, for diagnosing or treating additional pathophysiological conditions in animals. For example, substantially pure gp330, or a functional derivative thereof, may be administered to an animal to elicit a response characteristic of EGF, for example, improving the healing of wounds such as burns and abrasions. See U.S. Pat. No. 4,743,679 (1988).

One embodiment of this invention relates to a method for the treatment of wounds, comprising administering to an animal a pharmaceutical composition comprising:

(a) gp330, a functional derivative thereof, or a human analog thereof; and (b) a pharmaceutically acceptable carrier wherein said gp330, functional derivative thereof, or human analog thereof is present in an amount effective to treat the wound.

One of ordinary skill in the art can determine the amount of gp330, functional derivative thereof, or human analog thereof which is effective for the treatment of wounds with only routine experimentation.

Since EGF is also known to be a potent inhibitor of gastric acid secretion. See U.S. Pat. No. 4,743,679 (1988), European Patent Application, Publication No 0 177 915 (published 1986), and PCT Application Publication No. W085/00369. Therefore, gp330, a functional derivative thereof, or a human analog thereof is useful for the treatment or prevention of gastric ulcers.

This aspect of the invention relates to a method for the treatment or prevention of gastric ulcers in an animal, comprising administering to an animal a pharmaceutical composition comprising (a) gp330, a functional equivalent thereof, or a human analog thereof; and (b) a pharmaceutically acceptable carrier wherein said gp330, functional equivalent thereof, or human analog thereof is present in an amount effective to treat or prevent said ulcer.

One of ordinary skill in the art can determine the amount of gp330, functional derivative thereof, or human analog thereof which is effective for the treatment or prevention of gastric ulcers with only routine experimentation.

Individuals with Familial Hypercholesterolemia (FH) may be diagnosed by determining the presence of a mutation in the gene which codes for the LDL receptor. This may be accomplished screening fragmented DNA from a patient with recombinant cDNA encoding the LDL receptor protein. See U.S. Patent No. 4,745,060 (1988). Since cDNA clones encoding portions of gp330 shows 41 and 35% homology with the LDL receptor gene, gp330 cDNA, or fragments thereof, should also be useful in diagnosing patients having mutations in the LDL gene. Hybridization performed at the appropriate level of stringency, well known in the art, will permit genomic DNA from individuals with mutations in the LDL receptor gene to hybridize to gp330, or fragments thereof, more or less strongly than does DNA from a normal individual. Such altered hybridization allows detection of FH in patients.

One embodiment of this invention relates to a method for the detection a genetic abnormality involving the LDL receptor gene (e.g. FH) in an animal, comprising (a) isolating DNA from an animal suspected of having FH;

(b) fragmenting said DNA obtained in step (a) to give DNA fragments;

(c) separating the DNA fragments obtained in step (b);

(d) contacting said separated DNA fragments obtained in step (c) with detectably labeled gp330 cDNA, or a fragment thereof; and (e) detecting hybridization of the gp330 cDNA or fragment thereof with said separated DNA fragments.

The pattern of LDL gene fragments obtained from an individual suspected of having FH may be compared with the pattern obtained from a normal individual. If the pattern of LDL receptor gene fragments identified in the suspected individual exhibits an alteration relative to the control pattern, a genetic abnormality or mutation has been detected. Such genetic abnormalities may include point mutations, frame-shifts, deletions, insertions, inversions, etc., and are well known in the art.

According to this method, the DNA may be fragmented according to any method known to those of skill in the art, for example, by restriction enzyme digestion. The resulting DNA fragments may be separated, for example, by molecular weight using velocity sedimentation through a density gradient, or by molecular size using gel exclusion chromatography. Alternatively, the fragments may be separated by electrophoresis through an agarose or polyacrylamide gel matrix. The gp330 cDNA, or fragment thereof, may be detectably labeled with radionuclides which allow for ready visualization of the corresponding genomic LDL receptor DNA fragment pattern after hybridization and autoradiography. Other labelling techniques, including heavy isotopes, are also useful.

Having now generally described the invention, the same will be better understood by reference to specific examples which are presented herein for the purpose of illustration only and are not intended to limit the invention or any embodiment thereof.

EXAMPLES

EXAMPLE 1

Purification of gp330

A crude tubular rich fraction of normal rat kidneys (Fx1A) was prepared by a previously described method which involves sieving to remove glomeruli followed by differential centrifugation (Edgington, T. S. et al., *J. Exp. Med.* 127:555-572 (1968)). Using Fx1A at a protein concentration of 3 mg/ml, soluble membrane proteins (FxDOC) were extracted with 50 mM Tris.HCl, pH8.6, containing I mM phenylmethylsulfonyl fluoride (PMSF) and 1% sodium deoxycholate (DOC) for 1 hr on ice. FxDOC was separated from insoluble material by centrifugation at 27,000×g for 20 min.

Affinity purified rat gp330 was prepared from FxDOC with a monoclonal anti-gp330 antibody, 14CI (Bhan, A., et al., *Lab. Invest.* 53:421-432 (1985)), using the method of Schneider, C. et al., *J. Biol. Chem.* 257 10766-10768 (1982), as modified by Gluck, F. and Caldwell, J., *J. Biol. Chem.* 262:15780-15789 (1987).

Purified gp330 was analyzed on SDS-PAGE (Laemmli, U., *Nature* 227:680 (1970)) with a 4-12% acrylamide gradient under reducing and non-reducing conditions. Non-reduced fibronectin was used as a molecular weight marker. Gels were stained with Coomassie blue.

The monoclonal affinity purified gp330 showed a single, Coomassie-blue stained band with an apparent molecular weight of 440,000 under both reducing and non-reducing conditions.

EXAMPLE 2

Preparation of Rabbit Anti-gD330

A polyclonal rabbit anti-gp330 was prepared by immunizing New Zealand white rabbits with approximately 25 μg of affinity purified rat gp330 administered intradermally in complete Freund's adjuvant with boosting at 2 and 4 weeks with the protein in incomplete Freund's adjuvant. The animals were bled 2 weeks after the final injection.

The rabbit antisera were tested for reactivity with the immunogen by solid phase radioimmunoassay (RIA) according to Kamata, K. et al., *J. Immunol.* 135:2400–2408 (1985). The antisera reacted with the immunogen at a 1:10,000 dilution.

EXAMPLE 3

Preparation of Heymann Nephritis Glomerular Eluates

Kidneys were obtained from rats with active Heymann nephritis induced by immunization with rat Fx1A plus adjuvants according to Edgington, T. S. et al., *J. ExD. Med.* 127:555–572 (1968).

Glomerular eluates were prepared using a previously described method (Kamata, K., et al., *J. Immunol.* 135:2400–2408 (1985)). The tissue was finely minced, washed free of red blood cells with 0.01 M phosphate buffered saline (PBS), pH 7.3, and forced through stacked metal sieves. A glomerular rich fraction was obtained from the 200 mesh sieve, pelleted at 400xg for 5 min and washed with PBS containing 1nM PMSF until the supernatant was clear. After the final centrifugation, 0.02 M citrate buffer, pH 3.2, was added to give a 10% suspension. The suspension was placed on ice and sonicated under mild conditions, using a sonifier cell disrupter (Heat Systems-Ultrasonics, Inc., Plainview, Long Island, N.Y.). After incubation for 4 hr at 37° C., the suspension was centrifuged at 10,000×g for 20 min; the supernatant was recovered and the pH adjusted to pH 7.3 with the addition of 1 M Tris base. The eluate was concentrated by negative pressure ultrafiltration (Cx-10 immersible filter, Millipore Corp.; Bedford, Mass.) and dialyzed (Spectrapor 2, Spectrum Medical Industries, Los Angeles, Calif.) against 50×volume of PBS overnight at 4° C.

EXAMPLE 4

Cloning of gp330

A. Tryptic Cleavage of Heymann Nephritis Antigen

Tryptic peptide fragments of gp330 were prepared according to Wong, W. W. et al., *P.N.A.S. (USA)* 82:7711 (1985). Three nanomoles of purified gp330 in 7 M guanidine hydrochloride were reduced by treatment with dithiothreitol and alkylated with [$^{14}$C]-iodoacetic acid (Amersham, 56 Ci/mmol; 1 Ci=37 GBq) at 37° C. After precipitation of the radioalkylated protein with 4 vol. of acetone-methanol (50:50, vol./vol.), the protein was redissolved by heating for 15 min at 70° C. in 0.1 M NH$_4$HCO$_3$ with 0.2% Zwittergent 3-14 (Calbiochem-Behring) and cleaved overnight with L-1-tosylamido-2-phenylmethyl chloromethyl ketone (TPCK)-treated trypsin (E.C. 3.4.21.4; Cooper Biomedical, Malvern, Pa.) for 22 h at 37° C. Analysis by SDS-PAGE of 1% of the sample showed that no gp330 fragments of $M_r>20,000$ remained.

B. High Performance Liquid Chromatography (HPLC) of Tryptic Peptides

The gp330 tryptic peptides were purified according to Wong, W. W. et al., suora and Bennett, H. P. J. et al., *Biochem. J.* 168:9 (1977). After removing the NH$_4$HCO$_3$ by lyophilization, the peptides were resuspended in 200 μl of 6M guanidine hydrochloride in 0.1% trifluoroacetic acid (TFA) and separated by reverse phase high-pressure liquid chromatography (HPLC) using a Vydac phenyl column (25×0.46 cm) and a 120 min linear gradient of 0–60% acetonitrile in 0.1% TFA. Chromatographic peaks were collected manually and peptides were recovered by lyophilization. Selected fractions were purified by rechromatography. Peptides were detected by absorbance at 214 and 280 nm. Five peptides were purified by rechromatography for amino acid sequence analysis, identified as peptides 53, 54, 60, 74, and 77 (FIG. 1).

C. Protein Sequence Analysis

The amino acid sequences of tryptic peptides were determined by automated Edman degradation using an Applied Biosystem 470A Sequencer and a 120 Pth Analyser. The sequence of five of these peptides are depicted in FIG. 2.

D. Synthesis of a Degenerate Oligonucleotide Probe

A 23 base oligonucleotide with 16-fold degeneracy was synthesized corresponding to the first nine amino acids of the peptide #77 shown in FIG. 2 with an Applied Biosystems 380A DNA Synthesizer and purified by polyacrylamide gel electrophoresis. Deoxyinosine (I) was used as an "ambiguous codon position" (Ohtsuka, E. et al., *J. Biol. Chem.* 260:2605 (1985); Lathe, R., J. Mol. Biol. 183:1 (1985)) to reduce the degree of degeneracy from 256 to 16 fold. The synthetic oligonucleotide probe had the following sequence: TA(T/C)-TGG-GT(I)-GA(T/C)-GC(I)-TT(T/C)-TT(T/C)-GA.

E. Screening of λgt11 cDNA Library of Rat Kidney

A rat kidney λgt11 cDNA library (Clontech Laboratories Inc.; Palo Alto, Calif.) was screened with the rabbit anti gp330 antisera, as described by Huynh et al., DNA Cloning: A Practical Approach. D. M. Glover ed., IRL Press, Oxford 1:49 (1985). The rabbit antiserum was diluted to 1:1000 with TBST (50 mM Tris-Cl, pH 7.9+150 mM NaCl+0.05% Tween 20), 1% Bovine serum albumin (BSA), and 0.02% NaN$_3$, and used without further purification. The bound antibody was incubated with goat anti-rabbit antibody conjugated with horseradish peroxidase or biotinylated secondary antibody followed by avidin-biotin-horseradish peroxidase complex formation (Clontech Laboratories Inc.). 4-Chloro-1-naphthol was used as a substrate for peroxidase. Plaque purity was obtained on the third round of screening. Seven clones identified as immunoreactive were further examined and found to comprise 0.4, 0.48, 0.6, 1.2, 1.4, and two 2.4 kb gp330 DNA fragments.

F. Hybridization

The 23 base oligonucleotide was end-labelled by T4 polynucleotide kinase (New England Biolabs) with [γ-$^{32}$P] ATP (New England Nuclear) (Zoeller, M. and Smith, M., DNA 3:479 (1984)) to a specific activity of $10^8$ cpm/μg of DNA.

Total phage DNA was isolated from the immunoreactive clones (Maniatis, T., et al., *Molecular Cloning: A Laboratory Manual* Cold Spring Harbor Laboratory, Cold Spring Harbor, N.Y., pp. 363) and digested with EcoRI (New England Biolabs). DNA fragments were separated by electrophoresis in 1% agarose gel and transferred to Zetabind filters (Stratagene) as described by Southern, E., *J. Mol. Biol.* 98.503 (1975). The filter was prehybridized with a solution of 6xSSC, 5xDenhardts, 0.05% sodium pyrophosphate, 0.05% SDS and 100 μg/ml of herring sperm DNA at 42° C. overnight.

The filter was then allowed to hybridize with the radiolabelled oligonucleotide preparation in a solution containing 6xSSC, 1xDenhardts, 0.5% sodium pyrophosphate and 100 ug/ml of herring sperm DNA at 50° C. for overnight. The blot was washed twice at room temperature for 5 min with 6xSSC and 0.05% sodium pyrophosphate and once at 50° C. for 5 min and exposed on Kodak XAR film at −70° C. overnight.

The 1.4 Kb DNA fragment, which hybridized with the oligonucleotide probe, was gel purified and [α-$^{32}$P] dCTP (New England Nuclear) was incorporated into the fragment by nick-translation with a BRL (Bethesda Research Laboratories) nick-translation kit. Hybridization was also done with this nick-translated probe.

G. DNA Sequence Analysis

The gel purified cDNA inserts of EcoR1 digested positive clones were subcloned (Maniatis, T. et al., *Molecular Cloning: A Laboratory Manual*, Cold Spring Harbor Laboratory, Cold Spring Harbor, N.Y. 1982, pp. 390) in Bluescript (Stratagene, San Diego, Calif.). Plasmid DNA was isolated according to the method of Birnboim and Doly (*Nucl. Acids Res.* 7:1513 (1979)) and the DNA sequences were determined by the dideoxynucleotide chain termination method of Sanger, F. et al. (*Proc. Natl. Acad. Sci. (USA)* 74:5463 (1977).

The partial restriction maps of the inserts subcloned in Bluescript were obtained by single and double digestion with Acc1, Cla1, EcoR1, HindIII, and Pst1 restriction enzymes (New England Biolabs).

Figure 3:
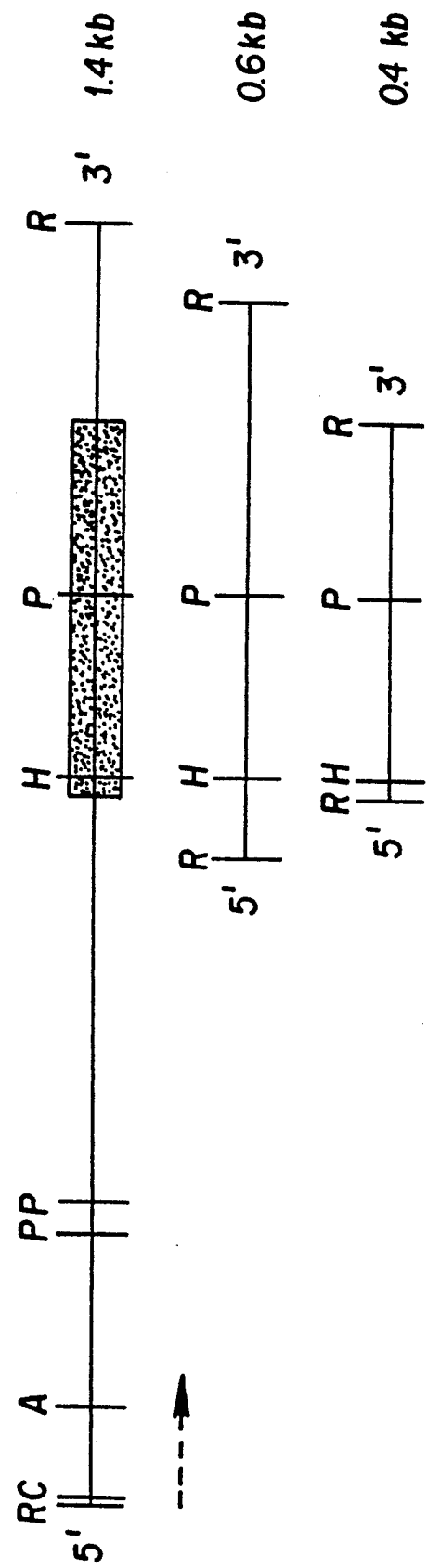
FIG. 3 depicts a restriction map of three gp330 DNA fragments (1.4, 0.6, and 0.4 kb). The small bar over the 5' end identifies the actual hybridization site for a 23-base oligonucleotide probe.

FIG. 3 shows the actual hybridization site (small bar at 5' end) for the elogonucleotide probe. This figure also shows that the three inserts have overlapping restriction maps.

EXAMPLE 6

Reaction of Partial gp330 Fusion Proteins With Eluted Antibodies From Heymann Naphritis Kidney Three fusion proteins, encoded by the partial clones displayed in FIG. 2, were produced using the plate lysate method of Bai et al., *J. Biol. Chem.* 261:12395 (1986). The phage clones and non-recombinant λgt11 were used to infect *Escherichia coli* Y1090. Phage were progagated on *E. coli* at 42° C. for 3.5 hr. Plates were overlayed with 0.8 ml of 5.0 mM isopropyl β-D-thiogalactopyranoside (IPTG) from Sigma) for another 3.5 hr at 37° C. An equal amount of water was used as control. After induction, plates were incubated for another 15 min with 0.8 ml of double strength Laemmli sample buffer (Laemmli, *Nature* 227:680 (1970)) at room temperature with gentle rotary shaking. The combined solutions were collected and 80 μl samples of the solubilized proteins were separated by electrophoresis on a 7.5% NaDodSO$_4$-polyacrylamide gels. One gel was stained with Coomasie blue for molecular weight determination. Proteins from other gels were electrophoretically transferred to nitrocellulose paper (Millipore) according to Towbin, H. et al., *Proc. Natl. Acad. Sci. (USA)* 76:4350 (1979) and allowed to react with polyclonal anti-gp330 antiserum (1:1000 dilution) and eluted with autoantibodies from Heymann nephritis kidneys (diluted to 0.5 ug IgG/ml), overnight with gentle shaking at room temperature after blocking the filter in buffer with 3% BSA. Goat anti-mouse IgG conjugated with horseradish peroxidase (Bio-rad) was used as secondary antibody with Heymann eluates.

Fusion proteins were immunoreactive with the polyclonal antiserum against gp330 as shown by immunoblot analysis. *E. coli* infected with recombinant λgtI1 produce small amounts of immunoreactive fusion protein without IPTG relative to *E. coli* raised with IPTG. There was no reaction with proteins from *E. coli* infected with non-recombinant λgt11.

Figure 5:
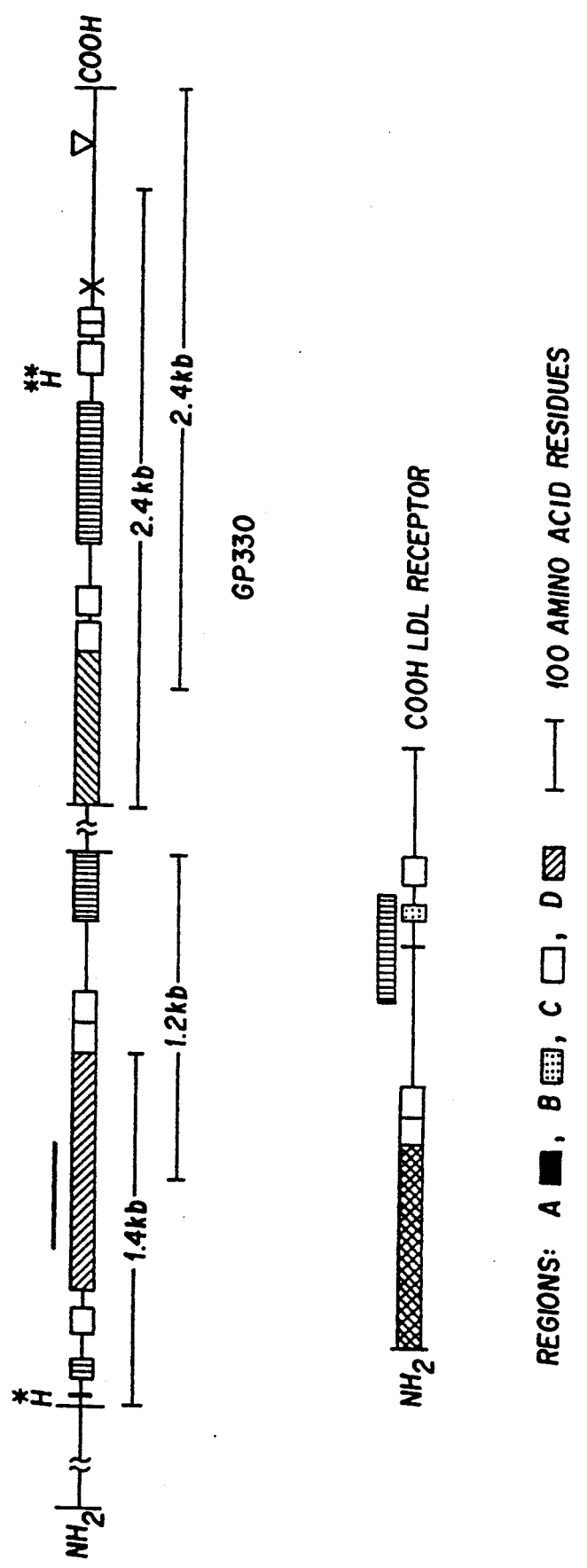
FIG. 5 depicts the comparative structures of gp 330 deduced from the nucleotide sequence of six partial cDNAs and the human LDL receptor. The location of two gp330 tryptic peptide sequences are indicated by segments marked with one or two asterisks. The protein sequence deduced from the 2.9 kb DNA sequence was obtained from two overlapping 2.4 kb clones, as depicted, and contains a 29-amino acid transmembrane segment (marked X) and a 188-amino acid cytoplasmic tail (stop codon marked as open triangle). Regions A to F correspond to the amino acid sequences shown in FIGS. 6 and 6A.
Figure 6:
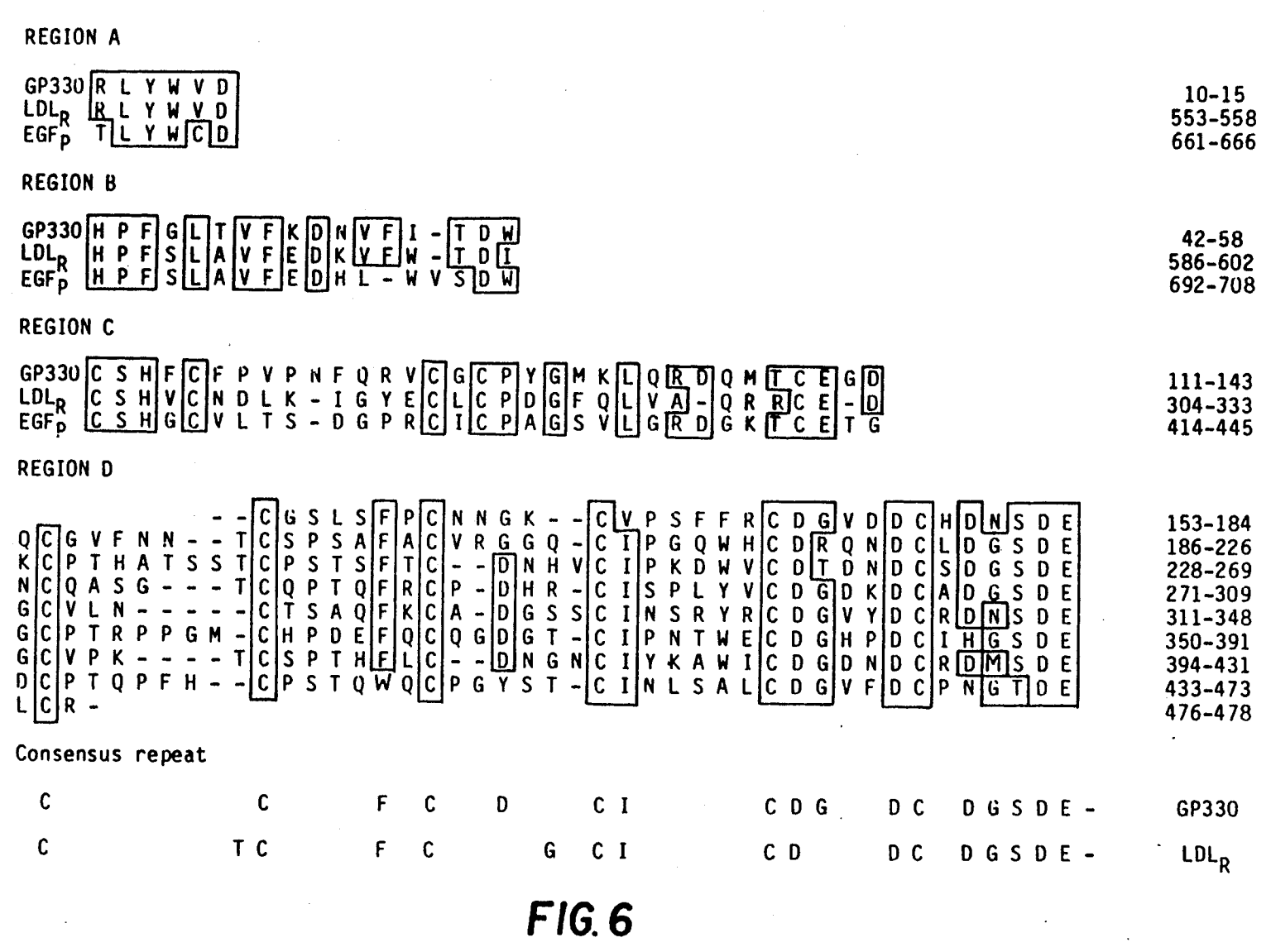
Figure 6A:
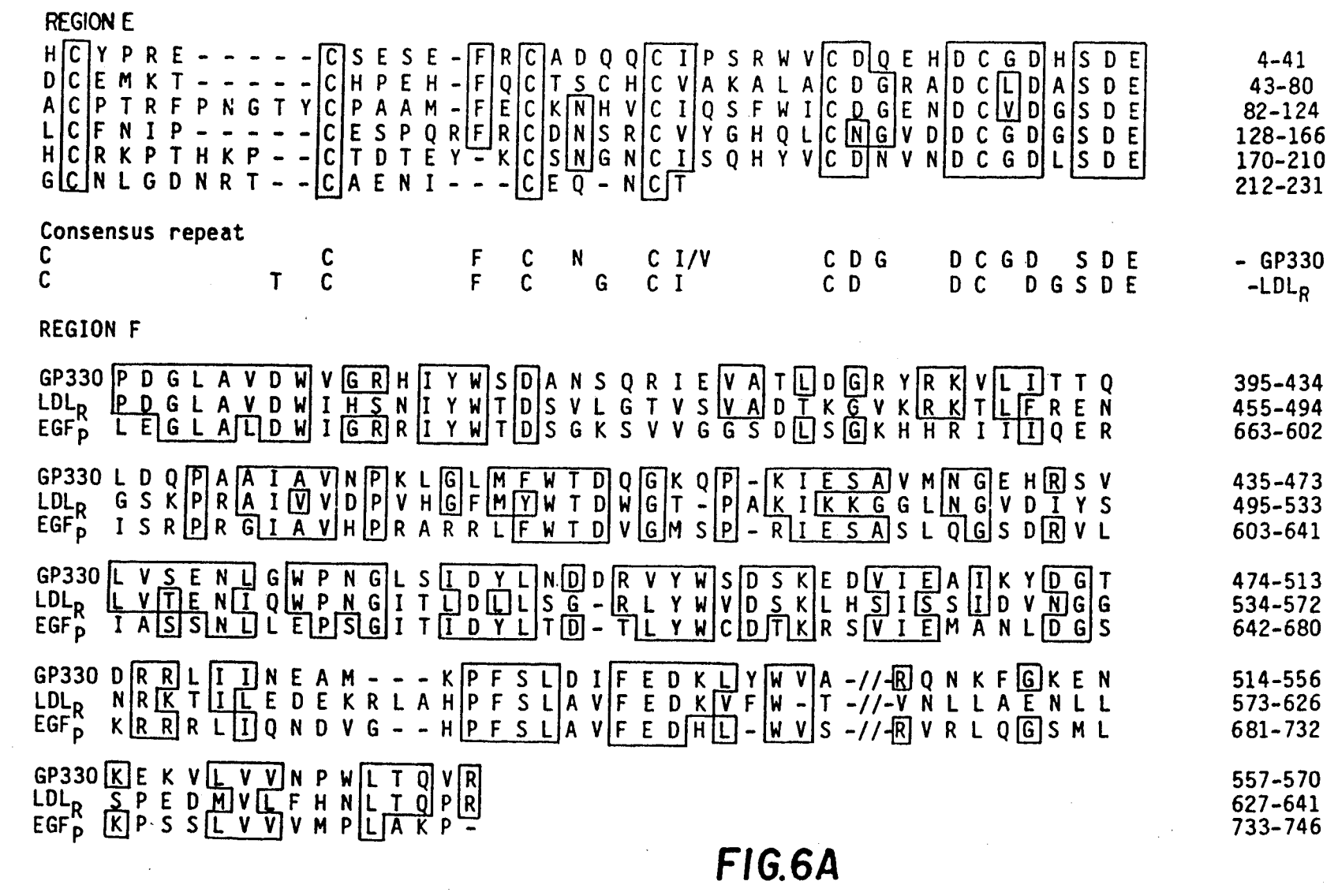
Figure 7A:
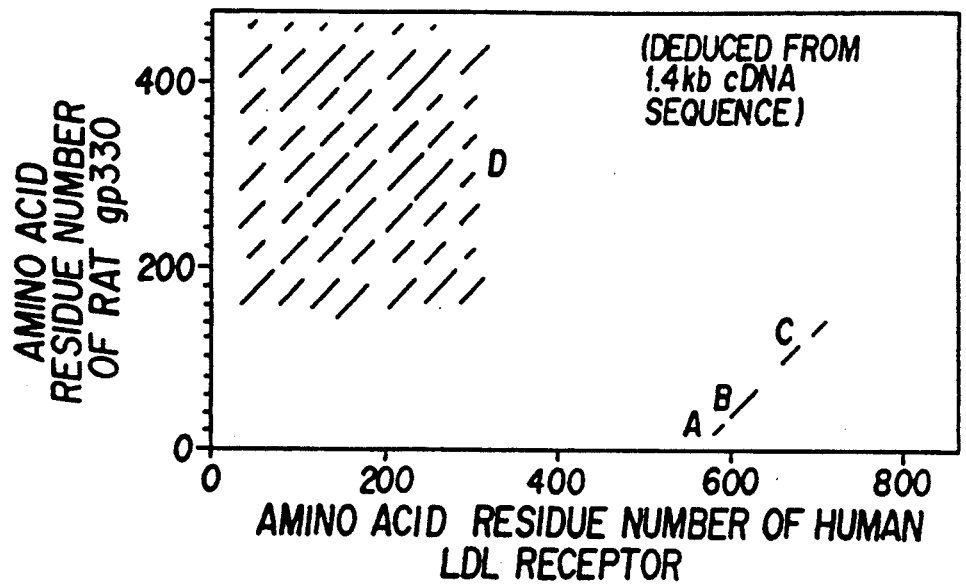
FIGS. 7A and 7B depict a dot matrix analysis of the amino acid sequences of rat gp330 and human $LDL_R$.
Figure 7B:
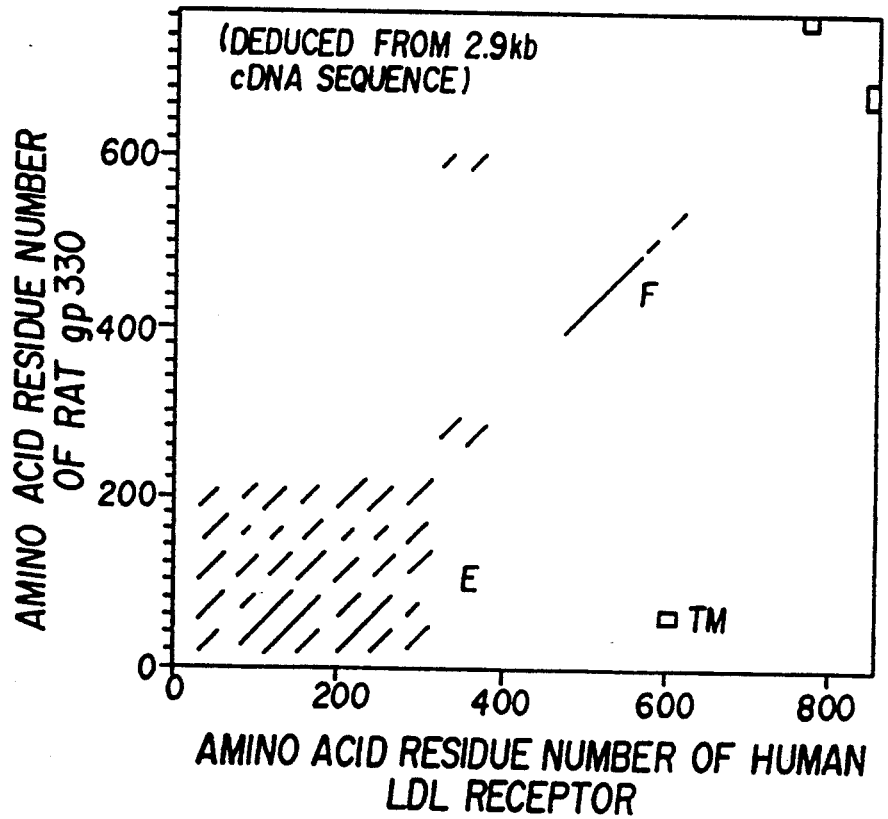

Western blot analysis of β-galactosidase fusion proteins with Heymann eluates showed strong reaction with the fusion proteins. Thus, each fusion protein contains at least one antigenic site recognized by the pathological autoantibodies. The 0.4 kb insert (FIG. 5, solid bar above region D) contains an immunoreactive site of gp330. Interestingly, region D contains eight LDL$_R$ consensus repeats (FIGS. 5, 6, 7 and 8). Further, since this region of gp330 is positioned NH$_2$-terminally (although the determination of its exact position in the gp330 molecule awaits the completion of the entire nucleotide sequence), it is likely that this antigenic site is displayed in a region of gp330 extending from the external surface of an epithelial cell membrane. Whether additional immunoreactive regions are present in the regions flanking this site remains unclear. Additional fusion proteins derived from the overlapping 2.4 kb inserts did not react with the autoantibodies, although each of these fusion proteins contains additional consensus repeats (FIGS. 5, 6 and 7, region E). Since the fusion proteins are not glycosylated, the antigenic sites must be on the protein component of gp330.

SUMMARY

In summary, rabbit polyclonal antisera raised against gp330 were used to screen a rat kidney λgt11 cDNA library allowing the isolation of partial cDNA clones of gp330 (0.4, 0.48, 0.6, 1.2, 1.4, and two 2.4 kb clones). The presence of the nucleotide sequence of the screening oligonucleotide at the 5' end of the 1.4kb insert proved that it is a partial cDNA clone of gp330. Further, the fusion protein expressed by three of these clones were strongly reactive with this antibody, indicating that the expressed proteins are part of gp330. Since the antibody is of polyclonal origin, some epitopes recognized might not make up part of the tissue antigen involved in immune complex formation in vivo.

In order to ascertain the epitopic specificity of the expressed fusion proteins, they were tested with eluates from the glomeruli of rats with Heymann Nephritis, which are known to contain autoantibodies specific for gp330. All of the fusion proteins strongly reacted with the Heymann nephritis autoantibodies. Restriction maps of these three clones suggested that one of the epitopes recognized by Heymann Nephritis autoantibodies must be encoded by DNA present at the region in which the clones overlap.

The fusion protein produced by the smallest insert is 130 kD. Since the apparent molecular weight of β-galactosidase is 116 kD, Heymann nephritis autoantibodies reacted with an epitope contained within a protein with an apparent molecule weight as small as 14 kD.

EXAMPLE 6

Comparison of the gp330 DNA Sequence with the Human LDL$_R$ and Mouse EGF$_p$ Sequences In order to determine whether the deduced gp330 partial sequences share protein sequence similarity with other proteins, computer-based searches were performed using the National Biomedical Research Foundation protein database and the FASTP program (Devereux, J., et al., *Nucl. Acids Res.* 12:387 (1984); Lipman, D. J., et al., *Science* 227:1435 (1985)). Protein sequence similarities were found among rat gp330, human LDL$_R$ (Yamamoto, T., et al., *Cell* 39:27 (1984)), mouse EGF$_P$ (Gray, A., et al., *Nature* 303:722 (1983); Scott, J., et al., *Science* 221:236 (1983)).

FIG. 6 depicts a comparison of the structure of gp330 deduced from the nucleotide sequences of the five partial cDNAs and human LDL$_R$. The clone represented in FIG. 8 did not overlap with any of the other five clones, and its location within the sequence has yet to be determined. The gp330 protein sequences of the two regions between the break marks have not been determined. The protein sequence of the region containing regions A-D was deduced from the nested cDNA sequences derived 0.4 kb, 0.6 kb, and 1.4 kb clones. The protein sequence of the gp330 carboxy-terminal sequence (containing regions E and F, a 29 residue transmembrane segment (marked X), and a cytoplasmic tail segment) was deduced from two partial cDNA clones containing partly overlapping 2.4 kb DNA sequences, which together yielded 2.9 kb of nucleotide sequence. The locations of two gp330 tryptic peptide sequences, determined by automated Edman degradation, are indicated by lines marked with one or two asterisks. Regions A-F correspond to the amino acid sequences shown in FIG. 6. The cross-hatched (i.e., superimposed diagonals) region in the LDL$_R$ corresponds to regions D and E in gp330. FIG. 6 depicts the amino acid sequence comparisons of rat gp330, human LDL$_R$, and mouse EGF$_P$. The one letter code for the amino acids is used. The numbering corresponds to the amino acid residue number of the published sequences (Yamamoto, T., et al., *Cell* 39:27 (1984); Scott, J., et al., *Science* 221:236 (1983)) or the amino acid residue number (i.e., the NH$_2$-terminal residue was assigned as 1) assigned to the gp330 sequences derived from the 1.4 kb (regions A-D) and the 2.9 kb (regions E and F) nucleotide sequences. Comparisons among the amino acid sequences of gp330, LDL$_R$, and mouse EGF$_P$ are shown in regions A-C and F (see FIG. 6). The sequences of the consensus repeats, containing approximately 40 amino acids each, are displayed in regions D and E. The gaps were inserted to optimize the alignments. A comparison of the consensus repeats for gp330 and LDL$_R$ are shown separately for regions D and E.

FIG. 7 depicts dot matrix analyses of the amino acid sequences of rat gp330 and human LDL$_R$ (Devereux, J., et al., *Nucl. Acids Res.* 12:387 (1984); Maizel, J. V., et al., *Proc. Natl. Acad. Sci. USA* 78:7665 (1981)). The protein sequences for gp330 were deduced from the 1.4 kb and the 2.9 kb (comprised of two overlapping 2.4 kb) cDNA sequences. The protein sequence of the human LDL$_R$ was according to Yamamoto et al., suora. The uppercase letters refer to the corresponding regions in FIG. 6. "TM" identifies the position of the transmembrane segment in both proteins.

The oligonucleotide probe hybridized to the 5' end of the 1.4 kb insert (line with one asterisk). The oligonucleotide-hybridizing region contained the coding sequence defined by the tryptic peptide, which is partially identical to LDL$_R$ (FIG. 6, region A). The DNA sequence of the 0.4 kb insert is entirely contained within the 0.6 kb insert, which in turn is entirely contained within the 1.4 kb insert. Two overlapping 2.4 kb inserts provided an additional 2.9 kb nucleotide sequence (FIG. 5, segment containing regions E and F). The protein sequence deduced from the 2.9 kb DNA sequence contained a sequence identical to another tryptic peptide, Val-Leu-Val-Val-Asn-Pro-Trp-Leu-Thr-Gln-Val (FIG. 5, line with two asterisks), as well as a 29 amino acid transmembrane segment (FIG. 5, marked X), and the carboxy-terminal portion of gp330. LDL$_R$ and gp330 are similar in eight separate regions (FIG. 6, regions A-F, plus the two consensus sequences in the 480 base pair segment of FIG. 8 which has not yet been positioned relative to the other gp330 sequences). Interestingly, gp330 and LDL$_R$ contain repetitive cysteine-rich consensus sequences (approximately 40 amino acid residues/repeat) in regions D and E (FIG. 6). At least 14 consensus repeats are distributed within the interstice of the gp330 molecule (FIG. 5, diagonals, plus two complete and two partial domains in FIG. 8), while the LDL$_R$ has eight consensus repeats positioned at its NH$_2$-terminus (Yamamoto, T., et al., *Cell* 39:27 (1984)) (FIG. 5, cross-hatched). Because LDL$_R$ and gp330 bear such marked similarity to one another, they may be members of the same gene family. Human complement protein C8 $\alpha$ and $\beta$ chains and C9 precursor also contain a single copy of the LDL$_R$ consensus repeat (Rao, A. G., et al., *Biochemistry* 26:3556 (1987); Howard, O. M. Z., et al., *Biochemistry* 26.3565 (1987); Stanley, K. K., et al., *EMBO J.* 4:375 (1985)). Furthermore, gp330, LDL$_R$, and EGF$_P$ displayed protein sequence similarities in non-repetitive regions (FIG. 6, regions A-C and F).

Having now fully described this invention, it will be appreciated by those skilled in the art that the same can be performed within a wide range of equivalent parameters without departing from the spirit and scope of the invention or any embodiment thereof.

What is claimed is:

1. A method for the detection of human DNA which contains the gene encoding low density lipoprotein receptor, said method comprising
   (a) isolating DNA that contains said DNA which contains the gene encoding low density lipoprotein receptor from a human;
   (b) contacting said DNA obtained in step (a) with DNA encoding gp330 under for a time and under conditions sufficient for hybridization to occur; and
   (c) detecting hybridization of said DNA which contains the gene encoding gp330 DNA with said low density lipoprotein receptor whereby the presence of said hybridization indicates the presence of DNA which contains the gene encoding the low density lipoprotein receptor.

* * * * *